United States Patent
Jones et al.

(10) Patent No.: US 10,445,560 B2
(45) Date of Patent: *Oct. 15, 2019

(54) PULSE WAVE DETECTION DEVICE AND PULSE WAVE DETECTION PROGRAM

(71) Applicant: EQUOS RESEARCH CO., LTD., Tokyo (JP)

(72) Inventors: Michael Jones, Tokyo (JP); Hideo Yamada, Tokyo (JP)

(73) Assignee: EQUOS RESEARCH CO., LTD., Tokyo (JP)

( * ) Notice: Subject to any disclaimer, the term of this patent is extended or adjusted under 35 U.S.C. 154(b) by 64 days.

This patent is subject to a terminal disclaimer.

(21) Appl. No.: 15/563,470

(22) PCT Filed: Mar. 30, 2016

(86) PCT No.: PCT/JP2016/060507
§ 371 (c)(1),
(2) Date: Sep. 29, 2017

(87) PCT Pub. No.: WO2016/159150
PCT Pub. Date: Oct. 6, 2016

(65) Prior Publication Data
US 2018/0068171 A1    Mar. 8, 2018

(30) Foreign Application Priority Data

Mar. 31, 2015  (JP) ................................. 2015-073963

(51) Int. Cl.
*G06K 9/00* (2006.01)
*A61B 5/00* (2006.01)
(Continued)

(52) U.S. Cl.
CPC ............ *G06K 9/00268* (2013.01); *A61B 5/00* (2013.01); *A61B 5/0013* (2013.01); *A61B 5/02* (2013.01);
(Continued)

(58) Field of Classification Search
CPC ......... G06K 9/00268; G06T 5/50; G06T 7/11; G06T 7/136; G06T 2207/10016
See application file for complete search history.

(56) References Cited

U.S. PATENT DOCUMENTS

| | | |
|---|---|---|
| 2007/0025722 A1 | 2/2007 | Matsugu et al. |
| 2009/0157482 A1 | 6/2009 | Jung et al. |

(Continued)

FOREIGN PATENT DOCUMENTS

| | | |
|---|---|---|
| EP | 2 893 872 A1 | 7/2015 |
| JP | 2003-348614 A | 12/2003 |

(Continued)

OTHER PUBLICATIONS

Feb. 16, 2018 Office Action issued in Japanese Patent Application No. 2015-073965.

(Continued)

*Primary Examiner* — Ruiping Li
(74) *Attorney, Agent, or Firm* — Oliff PLC

(57) ABSTRACT

A pulse wave detection device color converts a frame image of a moving image from RBG to HSV components, and identifies a skin section using the skin color of a user prepared in advance with an H component. The device converts the skin section of the image to YIQ components, and takes Qm as a pulse wave signal, Qm being obtained by averaging the Q values of the pixels. The device then obtains a chronological change in the pulse wave signal Qm and outputs the change as a pulse wave. Accordingly, it is possible to exclude disturbance factors from the pulse wave (Continued)

detection target, and successfully detect a pulse wave. The identification of the skin section is performed using the H component to identify candidate pixels, and using the S component to narrow down the candidate pixels to the target, so high-precision identification of the skin section is possible.

18 Claims, 27 Drawing Sheets

(51) Int. Cl.
| | |
|---|---|
| A61B 5/02 | (2006.01) |
| A61B 5/0245 | (2006.01) |
| G06T 1/00 | (2006.01) |
| G06T 7/00 | (2017.01) |
| G06T 7/136 | (2017.01) |
| G06T 7/11 | (2017.01) |
| A61B 5/1171 | (2016.01) |
| G06T 5/50 | (2006.01) |

(52) U.S. Cl.
CPC .......... *A61B 5/0245* (2013.01); *A61B 5/1176* (2013.01); *G06T 1/00* (2013.01); *G06T 5/50* (2013.01); *G06T 7/00* (2013.01); *G06T 7/11* (2017.01); *G06T 7/136* (2017.01); *G06T 2207/10016* (2013.01); *G06T 2207/10024* (2013.01); *G06T 2207/30088* (2013.01)

(56) References Cited

U.S. PATENT DOCUMENTS

| | | | |
|---|---|---|---|
| 2014/0079295 A1 | 3/2014 | Yoon et al. | |
| 2014/0086462 A1 | 3/2014 | Shan et al. | |
| 2014/0153800 A1 | 6/2014 | Kirenko et al. | |
| 2016/0228011 A1* | 8/2016 | Tsubaki | A61B 5/0077 |

FOREIGN PATENT DOCUMENTS

| | | |
|---|---|---|
| JP | 2007-096379 A | 4/2007 |
| JP | 2009-072438 A | 4/2009 |
| JP | 2009-213637 A | 9/2009 |
| JP | 2009-252243 A | 10/2009 |
| JP | 2010-239499 A | 10/2010 |
| JP | 2014-198201 A | 10/2014 |
| JP | 2014-198202 A | 10/2014 |
| JP | 2014-206785 A | 10/2014 |
| WO | 2014/038077 A1 | 3/2014 |

OTHER PUBLICATIONS

Oct. 4, 2018 Office Action issued in U.S. Appl. No. 15/563,409.
Sep. 17, 2018 Extended Search Report issued in European Patent Application No. 16773031.6.
Kakumanu et al; "A suvery of skin-color modeling and detection methods;" Pattern Recognition; vol. 40; pp. 1106-1122; 2007.
Sahindrakar; "Improving Motion Robustness of Contact-less Monitoring of Heart Rate Using Video Analysis;" TU/e University of Technology; Aug. 24, 2011.
Sep. 18, 2018 Extended Search Report issued in European Patent Application No. 16773032.4.
Jul. 17, 2018 Office Action issued in Japanese Patent Application No. 2017-510146.
Poh et al; "Advancements in Noncontact, Multiparameter Physiological Measurements Using a Webcam;" IEEE Transactions on Biomedical Engineering; vol. 58, No. 1 (2011); pp. 7-11.
Jun. 21, 2016 Search Report Issued in International Patent Application No. PCI/JP2016/060507.
Oct. 3, 2017 International Preliminary Report on Patentability Issued in International Patent Application No. PCT/JP2016/060507.
U.S. Appl. No. 15/563,409, filed Sep. 29, 2017 in the name of Jones et al.
Oct. 3, 2017 International Preliminary Report on Patentability issued in International Patent Application No. PCT/JP2016/060508.
Dec. 11, 2018 Office Action issued in Japanese Patent Application No. 2017-510146.
Jun. 6, 2019 Office Action issued in U.S. Appl. No. 15/563,409.

* cited by examiner

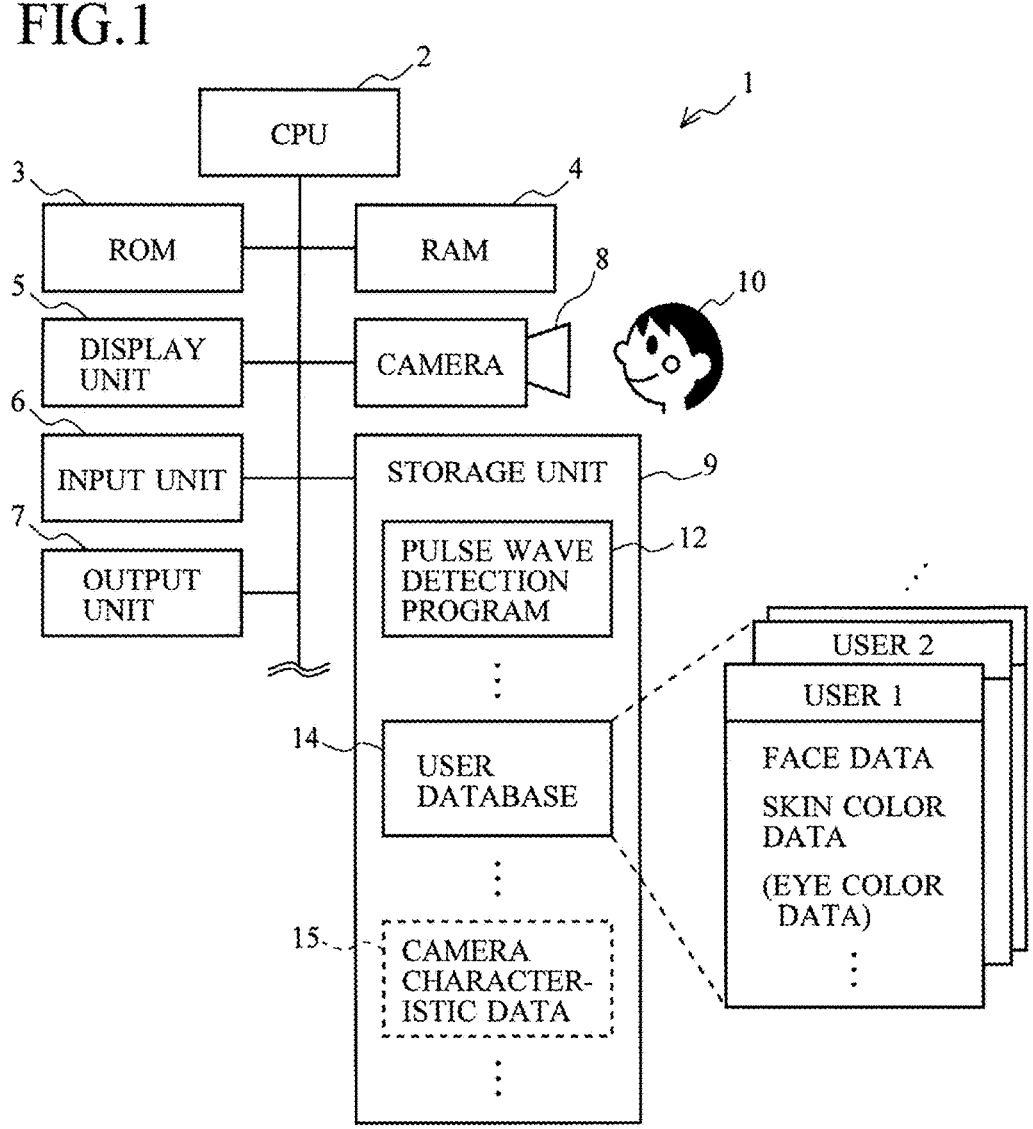

RGB SPACE

HSV SPACE

YIQ SPACE

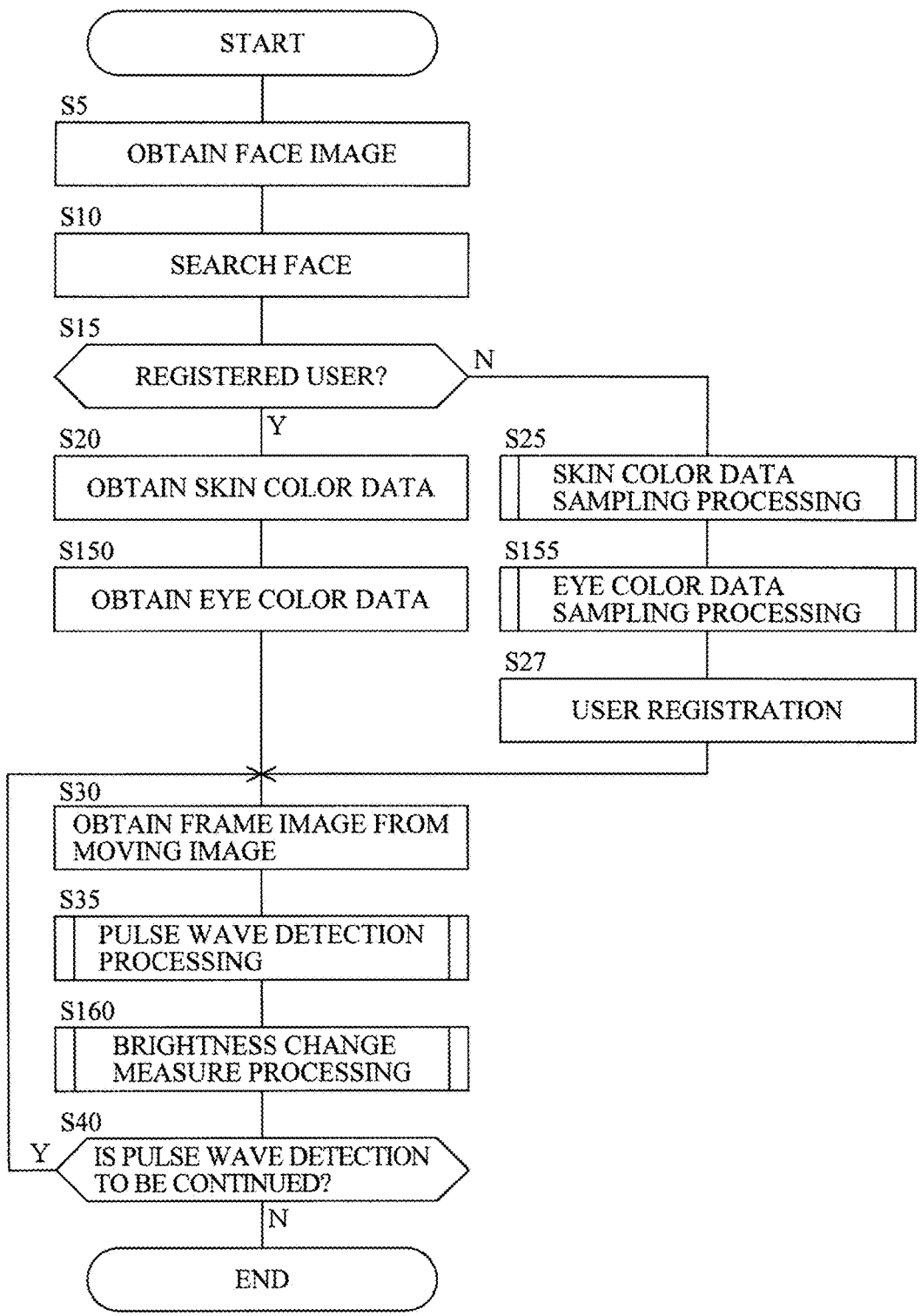

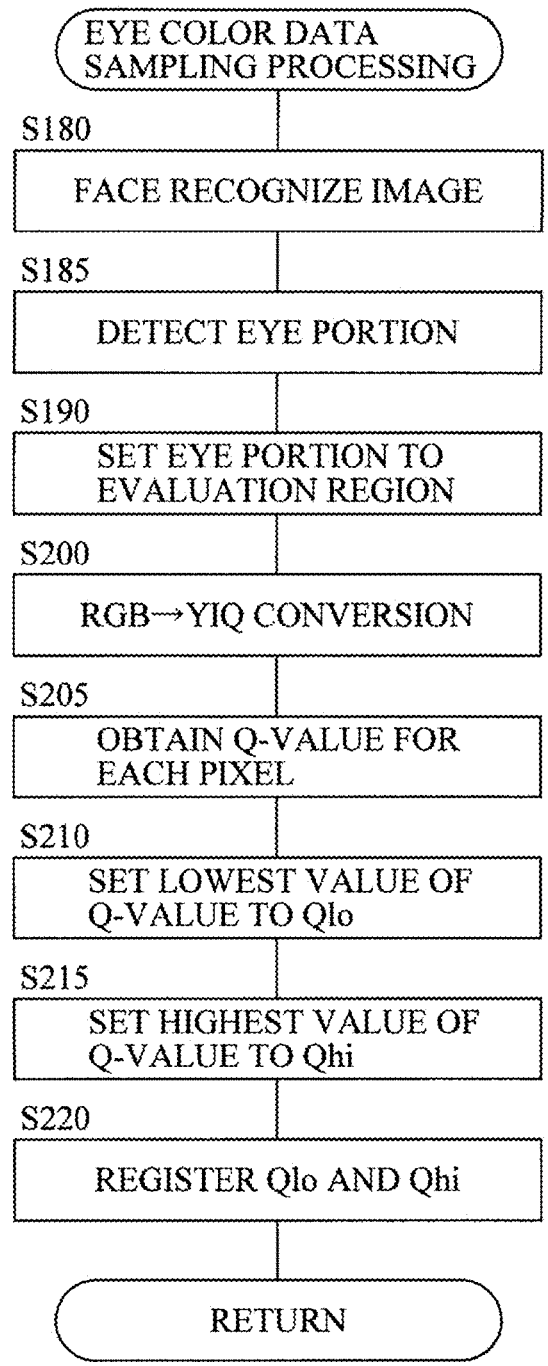

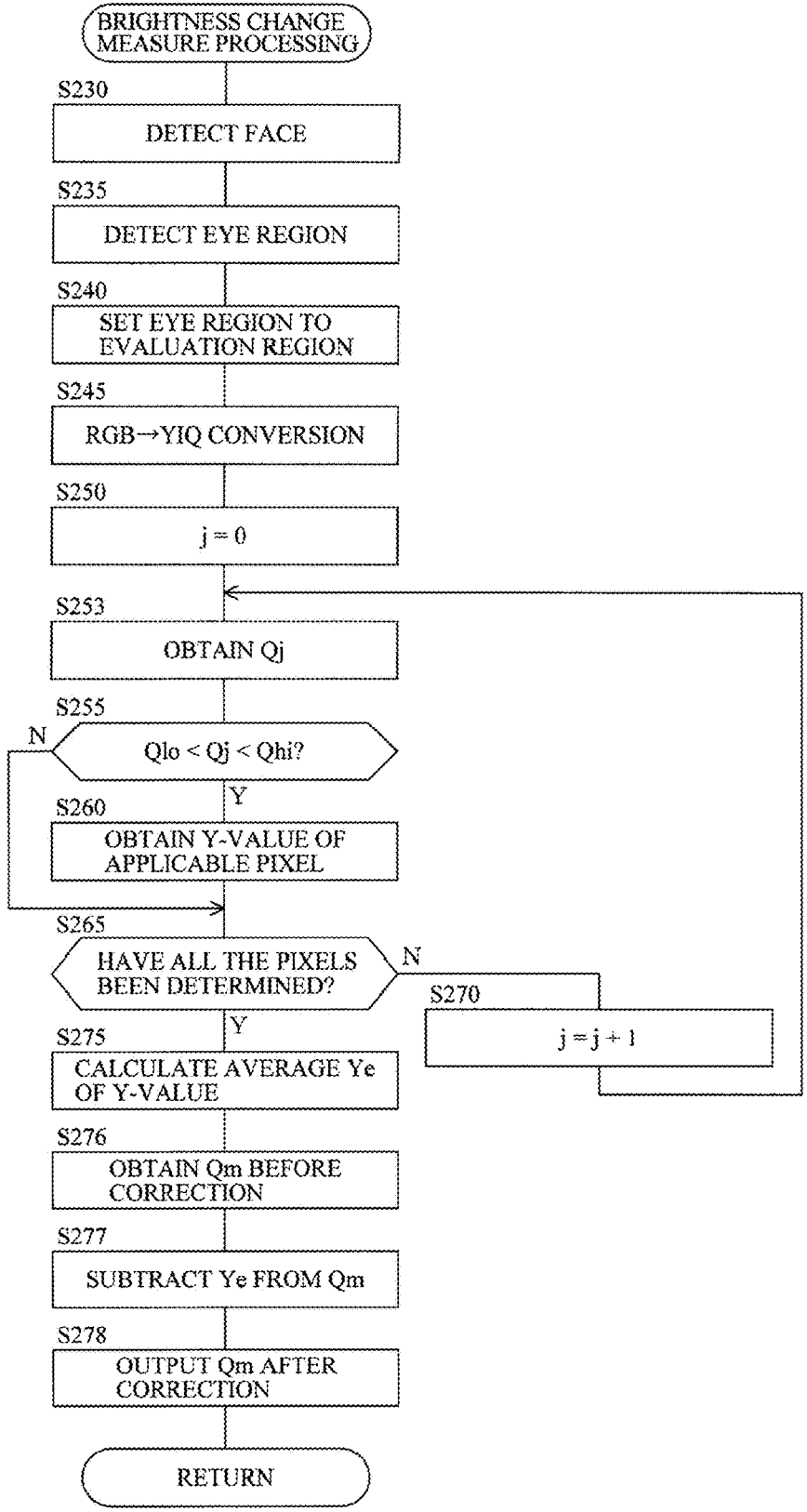

R COMPONENT    G COMPONENT    B COMPONENT

HSV IMAGE →
← POSITION OF SKIN PORTION

FIG.20(a)
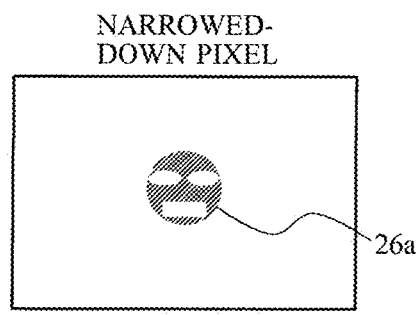
FIG.20(b)
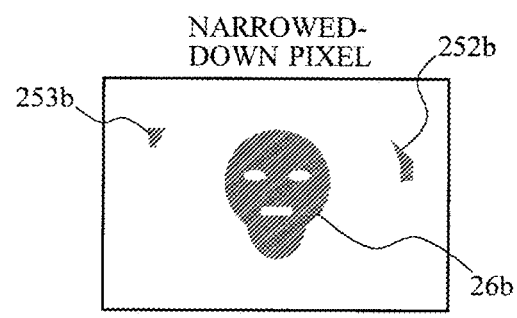
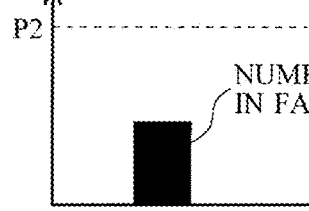
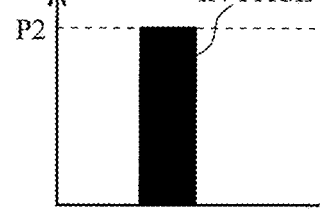
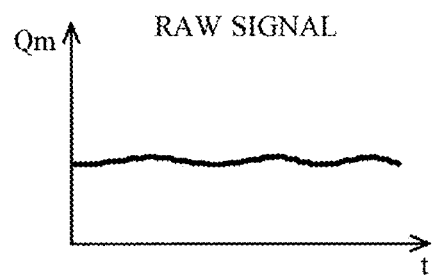
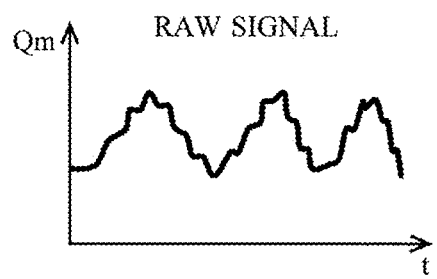

FIG.21(a)
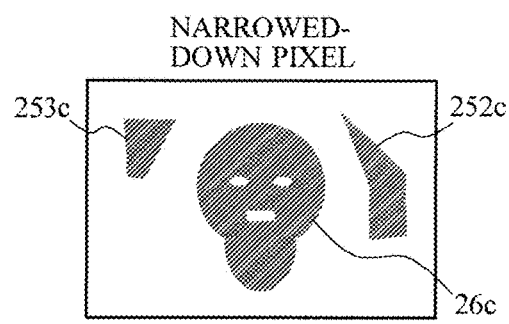
FIG.21(b)
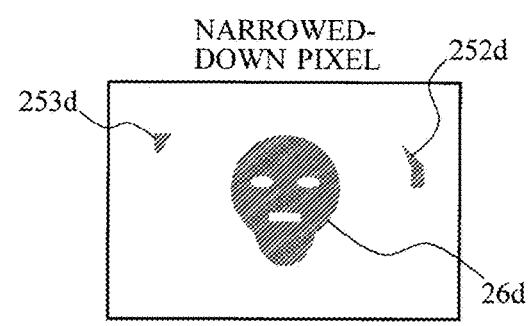
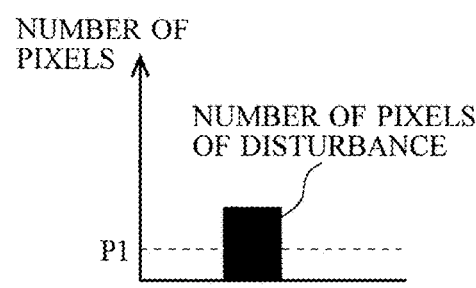 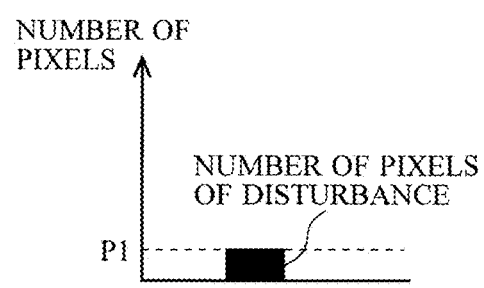
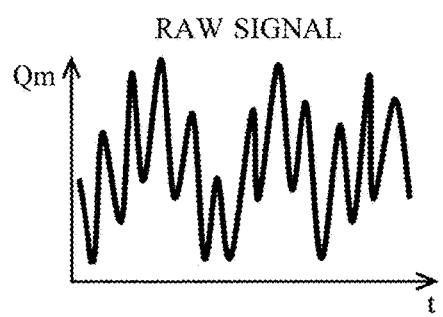 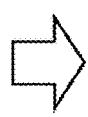 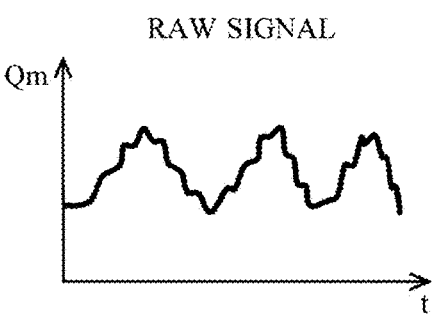

FIG.24(a) 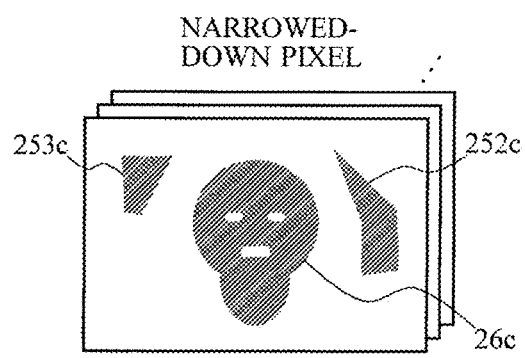 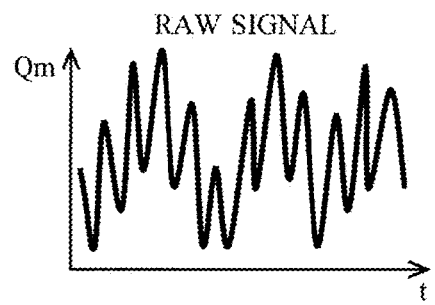 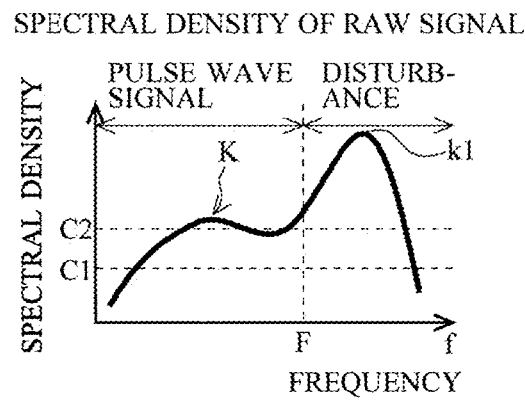
FIG.24(b) 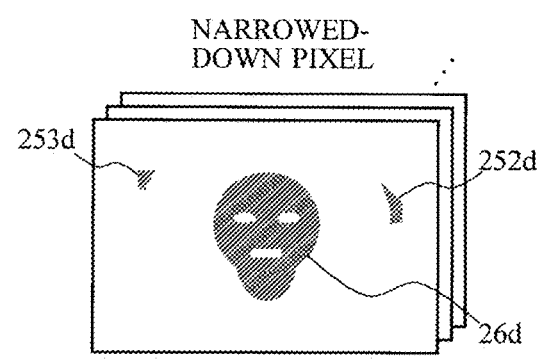 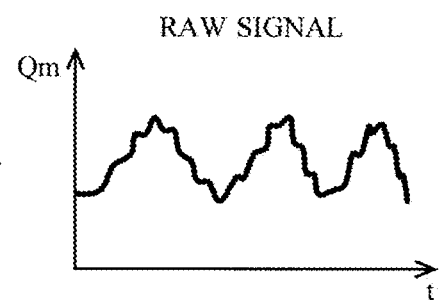 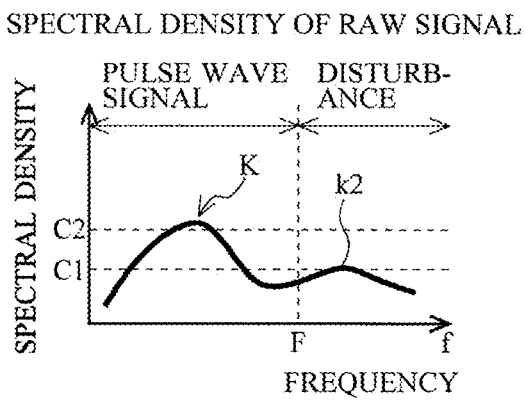

FIG.25(a)
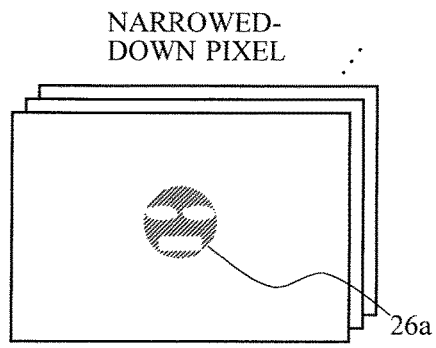
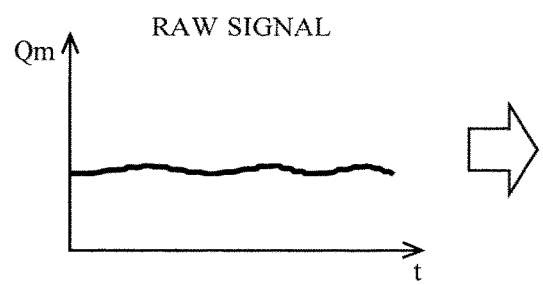
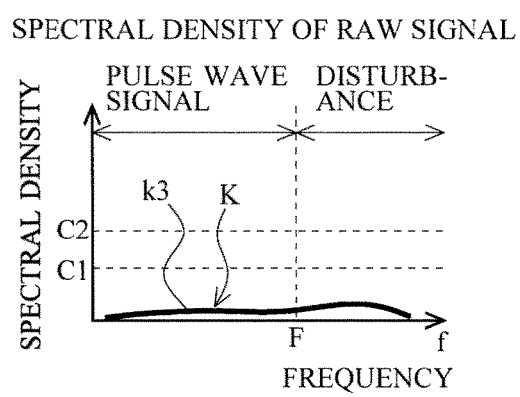
FIG.25(b)
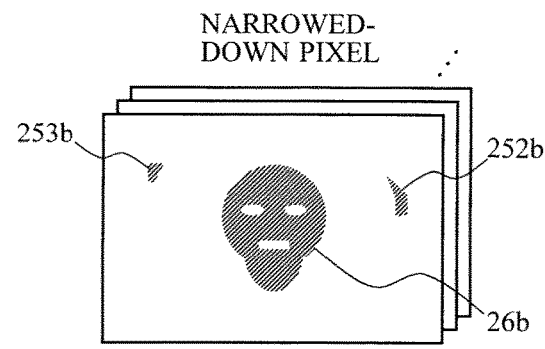
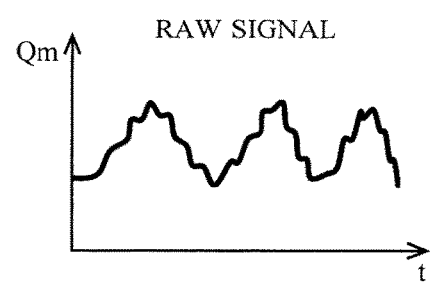
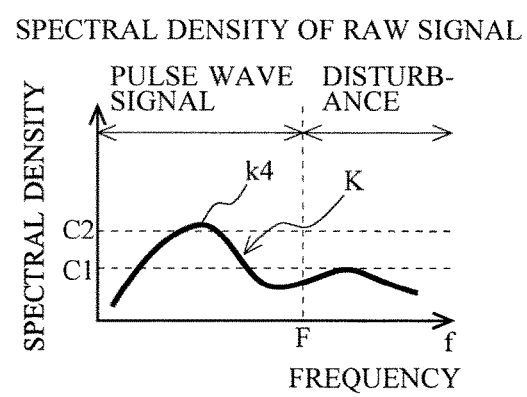

PULSE WAVE DETECTION DEVICE AND PULSE WAVE DETECTION PROGRAM

TECHNICAL FIELD

The present invention relates to a pulse wave detection device and a pulse wave detection program and relates to those detecting a pulse wave by using image processing, for example.

BACKGROUND ART

Detection of a pulse wave is extremely important in understanding a physiological state of a human being and a technology for detecting this from a remote place in a non-contact manner is in demand.

Such technologies include a study made by Massachusetts Institute of Technology which is a non-patent literature.

This technology detects a pulse wave by taking a moving image of the face of a subject by a web camera and analyzing the moving image by a laptop computer after the photographing (that is, not by real-time processing but by processing later).

This study realizes non-contact detection of a pulse wave by using an inexpensive general purpose device and a simple method against conventional detection of the pulse wave by using a special expensive device such as a laser and Doppler radar.

Here, an outline of this technology will be described by using FIG. 16.

First, as illustrated in FIG. 16(a), an evaluation region 101 having a rectangular shape is set on a screen of the moving image, the subject is seated so that the face of the subject is contained in the evaluation region 101, and the face in a still state is photographed in a moving image. The experiment is conducted indoors, and sunlight incident through a window is used as a light source.

By separating the obtained moving image into each of an R component, a G component, and a B component and averaging them, fluctuations on which the pulse waves is superimposed are obtained as illustrated in FIG. 16(b).

Each of these components include a pulse wave signal weighted in accordance with a light absorbing characteristic of hemoglobin or the like, and the pulse wave is obtained by conducting ICA (Independent Component Analysis) or the like on it.

The pulse wave is obtained from the moving image as above because, since a volume of a blood vessel is changed in accordance with heartbeats of the subject, an optical distance that the sunlight is transmitted through the skin is changed, and it appears as a change in reflected light from the face.

However, this technology is performed under an ideal environment of a laboratory, and there has been a problem that use in a practical scene such as detection of the pulse wave of a driver by mounting a pulse wave detection device on a vehicle is difficult due to various disturbance elements.

If a target of pulse wave detection moves, for example, the face of the target goes out of the evaluation region 101, whereby the pulse wave cannot be detected any longer.

Moreover, since a background 102 outside the face and a region where the pulse wave cannot be detected such as hair, eyes, eyebrows, mouth and the like are also included in the evaluation region 101, there is also a problem that detection accuracy lowers.

CITATION LIST

Non-Patent Literature

Non-Patent Literature 1: Advancements in Noncontact, Multiparameter Physiological Measurements Using a Webcam, Ming-Zher Poh, Daniel J. McDuff, and Rosalind W. Picard, IEEE Transactions on Biomedical Engineering, Vol. 58, No. 1, January 2011

DISCLOSURE OF THE INVENTION

Problem to be Solved by the Invention

The present invention has an object to conduct pulse wave detection with robustness against disturbance elements.

Means for Solving the Problem (1) In order to achieve above mentioned object, the invention described in claim 1 provides a pulse wave detection device comprising: moving image obtaining means for obtaining a moving image taking a region including at least skin of a target; skin portion specifying means for specifying a skin portion of the target shown on the obtained moving image; pulse wave obtaining means for obtaining a pulse wave of the target from a temporal change of predetermined color space components in the skin portion specified as above; and output means for outputting the obtained pulse wave.

(2) The invention described in claim 2 provides the pulse wave detection device according to claim 1, wherein the region including at least the skin of the target includes the face of the target.

(3) The invention described in claim 3 provides the pulse wave detection device according to claim 1 or 2, further comprising: reference component registering means for registering a reference component which is the color space component to be a reference for specifying the skin portion of the target, wherein the skin portion specifying means specifies a portion where the predetermined color space component corresponds to the registered reference component in the moving image as the skin portion.

(4) The invention described in claim 4 provides the pulse wave detection device according to claim 1, 2 or 3 wherein the color space component used by the skin portion specifying means for specifying the skin portion and the color space component used by the pulse wave obtaining means for obtaining the pulse wave are different color space components.

(5) The invention described in claim 5 provides the pulse wave detection device according to claim 4, wherein the color space component used by the skin portion specifying means for specifying the skin portion is a hue component (H) of an HSV color space made of the hue component (H), a saturation component (S), and a brightness component (V); and the color space component used by the pulse wave obtaining means for obtaining the pulse wave is a chromaticity component (Q) in a YIQ color space made of a brightness component (Y) and chromaticity components (I, Q).

(6) The invention described in claim 6 provides the pulse wave detection device according to any one of claims 1 to 5, further comprising: color space converting means for converting a color space of the moving image, wherein the skin portion specifying means and the pulse wave obtaining means obtain a color space component in the color space obtained by converting the obtained moving image by the color space converting means.

(7) The invention described in claim 7 provides the pulse wave detection device according to claim 3, further comprising: face image obtaining means for obtaining a face image taking a face of the target; and region specifying means for specifying a predetermined region where skin of the face is exposed by face recognition processing in the obtained face image, wherein the reference component registering means registers the color space component of the specified region as the reference component.

(8) The invention described in claim 8 provides the pulse wave detection device according to claim 7, wherein the predetermined region is a nose region of the target.

(9) The invention described in claim 9 provides the pulse wave detection device according to claim 7 or 8, wherein the reference component registering means registers a value obtained by applying statistical processing to distribution of the color space component in the specified region.

(10) The invention described in claim 10 provides the pulse wave detection device according to any one of claims 1 to 9, wherein the skin portion specifying means specifies the skin portion by the pixel values of the moving image.

(11) The invention described in claim 11 provides the pulse wave detection device according to any one of claims 1 to 10, wherein the target is a passenger of transportation equipment and monitoring means for monitoring a physical condition of the passenger by using the output pulse wave is provided.

(12) The invention described in claim 12 provides a pulse wave detection program for realizing by a computer: a moving image obtaining function for obtaining a moving image taking a region including at least skin of a target; a skin portion specifying function for specifying a skin portion of the target shown on the obtained moving image; a pulse wave obtaining function for obtaining a pulse wave of the target from a temporal change of the color space components in the specified skin portion; and an outputting function for outputting the obtained pulse wave.

(13) The invention described in claim 13 provides the pulse wave detection device according to claim 5, wherein the skin portion specifying means specifies the skin portion by specifying a skin portion candidate with the hue component (H) of the HSV color space and narrows down the skin portion candidate with the saturation component (S).

(14) The invention described in claim 14 provides the pulse wave detection device according to claim 13, wherein the skin portion specifying means specifies the skin portion for each frame image constituting the obtained moving image; and the pulse wave obtaining means obtains the pulse wave from a temporal change of the chromaticity component (Q) corresponding to the skin portion specified for each frame image.

(15) The invention described in claim 15 provides the pulse wave detection device according to claim 14, wherein the skin portion specifying means performs narrowing-down by using a lower limit value Slo and an upper limit value Shi of the saturation component (S) registered in advance.

(16) The invention described in claim 16 provides the pulse wave detection device according to claim 15, wherein the skin portion specifying means: sets the lower limit value Slo and the upper limit value Shi registered in advance to initial values; estimates a face region from the specified skin portion candidate; widens a range of the lower limit value Slo and upper limit value Shi when the number of pixels of the face region is less than a predetermined threshold value P2; performs the narrowing-down of the skin portion candidate again with the lower limit value and the upper limit value after widening; and repeats the narrowing-down again until the number of the pixels of the face region reaches the predetermined threshold value P2 or more.

(17) The invention described in claim 17 provides the pulse wave detection device according to claim 16, wherein the skin portion specifying means: narrows down the range of the lower limit value Slo and upper limit value Shi when the estimated number of pixels other than the face region is larger than a predetermined threshold value P1; performs the narrowing-down of the skin portion candidate again by the lower limit value and the upper limit value after narrowing-down; and repeats the narrowing-down again until the number of pixels other than the face region reaches the predetermined threshold value P1 or less.

(18) The invention described in claim 18 provides the pulse wave detection device according to claim 15, 16 or 17, further comprising: upper limit/lower limit value changing means for acquiring spectral density with respect to a temporal change of the chromaticity component (Q) for the plurality of frame images and for changing the lower limit value Slo and the upper limit value Shi registered in advance on the basis of a peak value of a predetermined frequency region with the spectral density, wherein the skin portion specifying means specifies the skin portion for the frame image and after by using the lower limit value Slo and the upper limit value Shi after being changed.

Effect of the Invention (1) According to the invention described in claim 1, accuracy of pulse wave detection can be improved since a disturbance element shown on a moving image is excluded and only a skin portion is taken out, a pulse wave can be detected therefrom.

(2) According to the invention described in claim 2, the pulse wave can be detected from the face which can be photographed easily since the skin is usually exposed.

(3) According to the invention described in claim 3, the skin portion can be easily extracted by comparison with a reference component.

(4) According to the invention described in claim 4, by employing a combination of color space components suitable for an observation target (since a target observed by light is different between the skin and the pulse wave), robustness against the disturbance element can be improved.

(5) According to the invention described in claim 5, by combining an H component found to be suitable in specification of the skin portion and a Q component found to be suitable for pulse wave detection, robustness against the disturbance element can be improved.

(6) According to the invention described in claim 6, by including color space conversion processing not in an external device but inside a pulse wave detection device, processing speed is improved, and the pulse wave can be detected from the moving image easily on a real time basis.

(7) According to the invention described in claim 7, by sampling a reference component of a color of the skin from the target himself/herself, a reference value including a subtle difference in skin color depending on a person can be easily obtained.

(8) According to the invention described in claim 8, the reference value of the color of the skin can be sampled from a region of a nose where the skin is exposed and spot specification is easy.

(9) According to the invention described in claim 9, biased distribution of the color of skin with a large individual difference can be averaged by statistical processing, whereby reliability of a reference component can be improved.

(10) According to the invention described in claim 10, a pixel acting as the disturbance element can be excluded from the evaluation target since the skin portion is extracted not from a region surrounded by a closed curve (where pixels not applicable to the skin portion are also scattered) but by the pixel values, whereby detection accuracy can be improved.

(11) According to the invention described in claim 11, a physical condition of a passenger onboard transportation equipment can be monitored.

(12) According to the invention described in claim 12, by spreading a pulse wave detection program and by installing it in a general-purpose computer, a pulse wave detection device can be configured easily and inexpensively.

According to the invention described in (13) to (18), the skin portion can be specified more accurately.

BRIEF DESCRIPTION OF THE DRAWINGS

FIG. 1 is a view illustrating configuration of a pulse wave detection device.

FIG. 9 is a flowchart for explaining a procedure of entire processing in a second embodiment.

FIG. 10 is a flowchart for explaining a procedure of eye color data sampling processing.

FIG. 11 is a flowchart explaining a procedure of brightness change measure processing.

FIG. 20 are a principle explanatory view of first adjustment processing in a case where a measurement region is small.

FIG. 21 are a principle explanatory view of the first adjustment processing in a case where there are many disturbances.

FIG. 24 are a principle explanatory view of second adjustment processing in a case where a peak value of the disturbance is large.

FIG. 25 are a principle explanatory view of the second adjustment processing in a case where a peak value of a pulse wave is small.

Figure 2A:
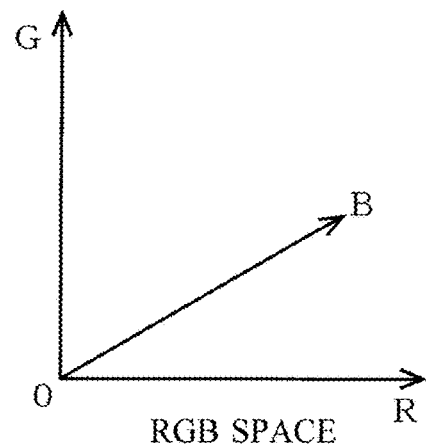
FIG. 2 are a view for explaining a color space.

DESCRIPTION OF THE EMBODIMENTS (1) Outline of Embodiments

In a first embodiment, a pulse wave detection device 1 color converts a frame image of a moving image from RGB components to HSV components and specifies a skin portion by using a skin color of a user prepared in advance with an H component. The H component is used because robustness is improved by using the H component in specification of the skin.

Subsequently, the pulse wave detection device 1 converts the skin portion of the frame image to YIQ components and takes Qm obtained by averaging a Q value of each pixel as a pulse wave signal. The Q component is used because robustness is improved by using the Q component for detection of the pulse wave signal.

The pulse wave detection device 1 obtains a chronological change of the pulse wave signal Qm by applying the processing described above to each frame image and outputs it as a pulse wave.

As described above, since the pulse wave detection device 1 can set the skin portion in the moving image to the evaluation region (ROI: Region of Interest), it can favorably detect the pulse wave by excluding the disturbance elements such as a background from pulse wave detection targets.

In a second embodiment, the pulse wave detection device 1 color converts frame image in the moving image the RGB components to the YIQ components and specifies the eye portion by using an eye color of the user prepared in advance with the Q component.

Then, the pulse wave detection device 1 detects brightness of a photographing environment with the Y value of the eye portion. Since the pulse wave signal does not appear in the eye portion, it can be used as a detection target of brightness.

Subsequently, the pulse wave detection device 1 detects the pulse wave signal Qm from an average of the Q values of the skin portion in the frame image and corrects a change of the brightness by subtracting an average value Ye of the Y values of the eye portion from this and outputs Qm after brightness correction.

As a result, even if the brightness changes since the user moves by a vehicle or the like, the pulse wave can be detected favorably.

In a third embodiment, the pulse wave detection device includes camera characteristic data for correcting fluctuation in characteristics of the pixel caused by the camera characteristics. Then, the Q value of the skin portion in the frame image is corrected by the camera characteristic data.

The pulse wave detection device 1 updates the camera characteristic data by using a change in the Q value of the skin portion caused by movement of the skin portion in the image.

Moreover, the pulse wave detection device 1 limits a color as a correction target to the skin color, which makes complicated algorithm or calculation unnecessary, and a calculation load is reduced, and real-time processing of the moving image can be executed favorably.

(2) Details of Embodiments

First Embodiment

FIG. 1 is a view illustrating configuration of the pulse wave detection device 1 according to this embodiment.

The pulse wave detection device 1 is mounted on a vehicle, for example, and monitors a pulse wave of a passenger (a driver or a passenger on a seat next to the driver's) and grasps physiological states such as a physical condition or a tensed state of the driver.

Moreover, the device can be used for detecting/monitoring a pulse wave of a patient or a victim at a medical site or a disaster site.

The pulse wave detection device 1 includes a CPU (Central Processing Unit) 2, a ROM (Read Only Memory) 3, a RAM (Random Access Memory) 4, a display unit 5, an input unit 6, an output unit 7, a camera 8, a storage unit 9 and the like and detects (or estimates) the pulse wave of a user 10 (a target of pulse wave detection).

The CPU 2 is a central processing unit for executing various types of information processing or control in accordance with programs stored in the storage unit 9 or the ROM 3.

In this embodiment, a moving image taken by the camera 8 is subjected to image processing, and the pulse wave of the user 10 is detected.

The ROM 3 is a read only memory and stores basic programs and parameters for operating the pulse wave detection device 1.

The RAM 4 is a memory capable of reading/writing and provides a working memory when the CPU 2 is operated.

In this embodiment, it extends and stores a frame image (still image of one frame) constituting the moving image or stores a calculation result so as to support the CPU 2 to detect the pulse wave from a portion of the skin (hereinafter referred to as a skin portion) in a frame image.

The display unit 5 is constituted by using a display device such as a liquid crystal screen and displays information required for operation of the pulse wave detection device 1 such as an operation screen of the pulse wave detection device 1 or display of a pulse wave.

The input unit 6 is constituted by using an input device such as a touch panel installed by overlapping the display device and receives an input of various types of information from presence of a touch on the screen display.

The output unit 7 is an interface for outputting various types of information to an external device and can output a detected pulse wave, can output a pulse obtained from a pulse wave or can output an alarm when a change appears in the pulse wave.

Moreover, the output unit 7 can make an output to another control device such as a controller for controlling a vehicle. The control device which received an output of a pulse wave or a heartbeat from the output unit 7 determines sleepiness or a tensed state of the driver (which will be described later), for example, and can perform control for the driver such as control of vibrating a steering wheel or a seat for awakening the sleepiness and an output of an alarm sound or a message, for example. Moreover, as control for the vehicle, at least any one of inter-vehicle distance control, vehicle speed control or brake control can be executed in accordance with the tensed state of the driver determined on the basis of the pulse wave. For example, if the control device determines that the driver is in a highly tensed state exceeding a predetermined value, it executes control such that the inter-vehicle distance is taken larger than a reference value, executes control such that a vehicle speed drops to a predetermined vehicle speed or less and executes deceleration processing by an automatic braking operation or the like if the vehicle speed is at the predetermined vehicle speed or more.

The camera 8 is constituted by using an optical system including a lens and an image sensor for converting an image formed by that to an electric signal and is installed so that the vicinity of the face of the user 10 comes to a photographing screen.

As the camera 8, an expensive one can be used, but a general-purpose product such as a web camera is used for the pulse wave detection device 1.

Since the pulse wave detection device 1 can detect the pulse wave favorably even with the camera 8 of a general-purpose product, a cost can be reduced.

The camera 8 takes a photo of a subject at a predetermined frame rate and outputs a moving image constituted by these continuous frame images (still images).

The frame image is constituted by an array of pixels which are minimum units constituting an image, and each pixel is color arranged by color components (R-value, G-value, B-value) of an RGB space.

The storage unit 9 is constituted by using a storage medium such as hard disk, an EEPROM (Electrically Erasable Programmable Read-Only Memory) and the like and stores programs and data for the CPU 2 to detect the pulse wave.

The storage unit 9 stores a pulse wave detection program 12, a user database 14, camera characteristic data 15 and the like.

The camera characteristic data 15 in them is data used in a third embodiment and will be described later.

The pulse wave detection program 12 is a program for causing the CPU 2 to execute the pulse wave detection processing.

The CPU 2 specifies the skin portion of the user in the moving image and detects a pulse wave from the specified skin portion by executing the pulse wave detection program.

The user database 14 is a database registering users using the pulse wave detection device 1.

The user database 14 stores registration data for each user such as a user 1, a user 2, . . . and the like.

Then, in the registration data, information specific to the user such as face data, skin color data, eye color data, . . . is registered.

The face data is feature of the face of the user made into data and is used for identifying the user seated in front of the camera 8 by face recognition.

The skin color data is data to be a reference of the color of the skin for specifying the skin portion of the user in the frame image. The skin portion is specified by comparison between the frame image and the skin color data.

The eye color data is data used in a second embodiment and will be described later.

FIG. 2 are a view for explaining the color space.

The pulse wave detection device 1 converts the color space of the frame image when detecting a pulse wave (it is called color conversion), and first, this will be explained.

A color image in general is expressed by three color components. In more detail, color information accompanying each pixel of an image is expressed as a coordinate value of a point in the color space extended using the three color components as axes.

In a general-purpose video camera, an R-component, a G-component, and a B-component of the RGB space are used as color components in many cases, and in the prior-art technologies, too, the R-, G-, and B-components included in the video signal are used as they are for pulse wave detection.

On the other hand, the inventor of the present application searched a more robust (resistant) color component against the disturbance elements.

As a result, it was found that the H component of an HSV space is suitable for specification of the skin portion, and the Q component in a YIQ space is suitable for pulse wave detection.

Thus, in the pulse wave detection device 1, the color component is used separately in accordance with the purpose.

As described above, since a reflection characteristic of the light is different depending on the observation targets, robustness against the disturbance can be further improved by selecting an optimal combination.

FIG. 2(a) is a view illustrating the RGB space.

The RGB space is constituted by an R-axis, a G-axis, and a B-axis representing RGB components and orthogonal to each other.

In the RGB space, color information is expressed by an R-value (red), a G-value (green), and a B-value (blue), and the RGB values of a pixel are specified by coordinate values of a point in the RGB space.

The RGB form is the most common color model, and the camera 8 also outputs a moving image in the RGB form.

Figure 2B:
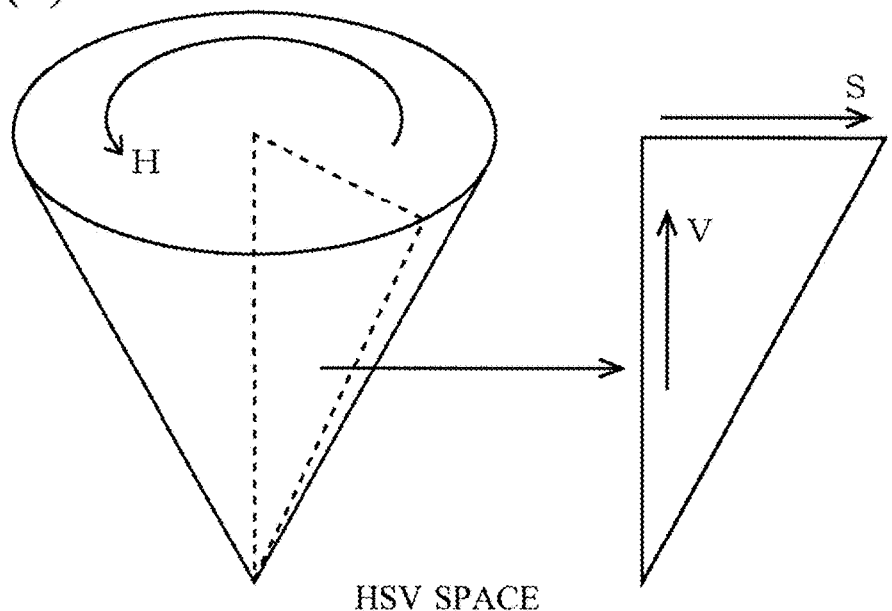

FIG. 2(b) is a view illustrating the HSV space.

The HSV space is expressed by a cone having a circular bottom surface, in which a rotation angle in a conical surface direction represents an H-component, a distance from a center in the bottom surface for an S-component, and a distance of a perpendicular line from a top of the cone to the bottom surface for a V-component.

In the HSV space, color information is expressed by an H-value (hue), an S-value (saturation), and a V-value (brightness), and an HSV value of a pixel are specified by coordinate values of a point in the HSV space.

The HSV form is used mainly in computer graphics.

The HSV space can be also expressed by a column in addition to the case expressed by a cone illustrated in FIG. 2(b). In this case, too, similar to the case expressed by a cone, a hue (H) changes along the outer periphery of the column, the saturation (S) changes with a distance from the center, and the brightness (V) changes from the top toward the bottom.

Figure 2C:
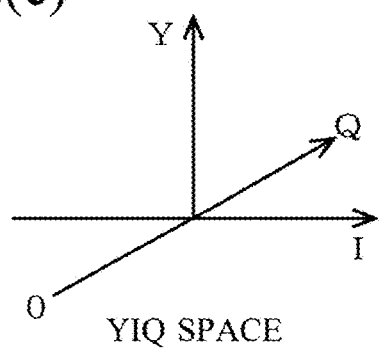

FIG. 2(c) is a view illustrating the YIQ space.

The YIQ space is constituted by a Y-axis, an I-axis, and a Q-axis representing YIQ components and orthogonal to each other.

In the YIQ space, color information is expressed by a Y-value (brightness), an I-value (chromaticity: warm color system), and a Q-value (chromaticity: cool color system), and a YIQ value of pixel is specified by a coordinate value of a point in the YIQ space.

The Y-value takes a positive value, and the I-value and the Q-value can take positive/negative values.

The YIQ form is used mainly in a video device as a form of a component signal generating an NTSC signal.

FIG. 3 are a view for explaining a mechanism for detecting a pulse wave from the moving image.

Figure 3A:
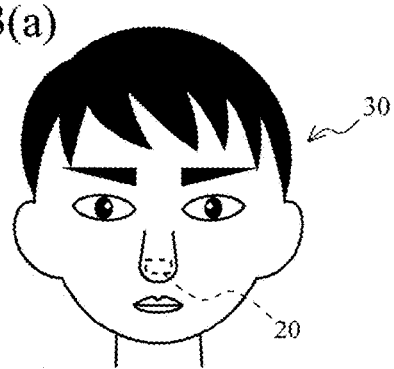
FIG. 3 are a view for explaining a mechanism for detecting a pulse wave from a moving image.

FIG. 3(a) is a view illustrating a method that the pulse wave detection device 1 samples skin color data from the face of the user.

The pulse wave detection device 1 takes a still image 30 of the face of the user by the camera 8, detects the nose and sets a nose region 20. Detection of the nose is made by using a general face recognition technology.

Then, the pulse wave detection device 1 converts the color space of the nose region 20 from the RGB space to the HSV space and generates skin color data from the H-value of each pixel.

The region where the skin color data is sampled is set to the nose region 20 because it can be specified easily by face recognition and a standard skin color is exposed.

Other than the nose, the skin color data can be sampled from the other regions such as a forehead and a cheek, for example.

Figure 3B:
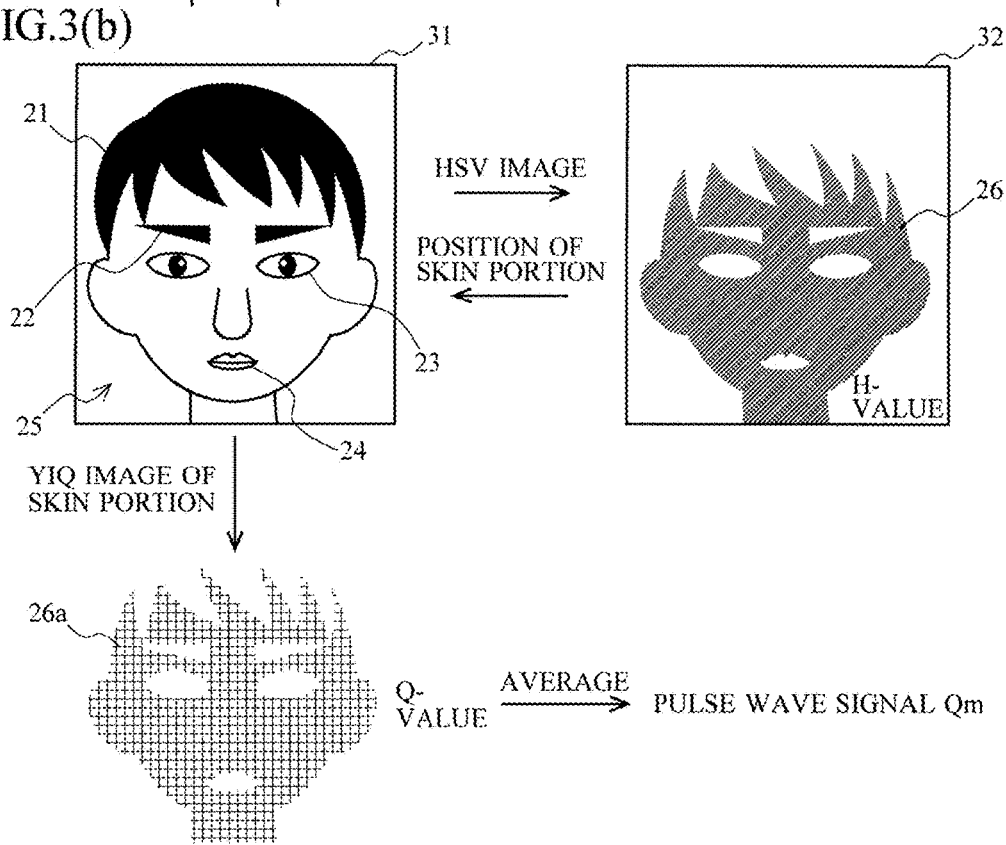

FIG. 3(b) is a view for explaining a method of extracting a pulse wave signal from the frame image 31.

In the frame image 31, hair 21, an eyebrow 22, an eye 23, a lip 24, a background 25 and the like are shown.

These portions other than the skin are portions which do not include a pulse wave signal or are not suitable for detection of the pulse wave signal and act as disturbance elements incurring accuracy drop in the pulse wave detection processing.

Thus, the pulse wave detection device 1 generates an HSV image 32 by color converting the frame image 31 and specifies a portion corresponding to the skin color data as a skin portion 26.

The skin portion 26 is specified by the pixel values and all the portions such as a neck where the skin is exposed are specified.

As described above, by ensuring the portion including the pulse wave signal to the maximum while excluding the disturbance elements, the pulse detection accuracy can be improved.

The pulse wave detection device 1 extracts the skin portion in the frame image 31 from a position of the skin portion 26 in the HSV image 32 and converts it to a YIQ image. As a result, a skin portion 26a in the YIQ space is obtained.

The pulse wave detection device 1 calculates Qm by averaging the Q-values of the pixels of the skin portion 26a and outputs Qm as a pulse wave signal.

It is to be noted that, in this embodiment, the frame image 31 is converted to the YIQ image and the skin portion 26a is obtained, but the skin portion 26a can be also obtained by converting the skin portion 26 in the HSV image 32.

Figure 3C:
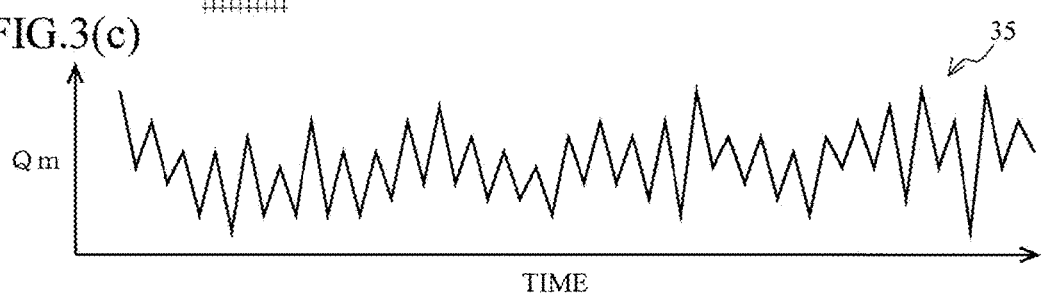

FIG. 3(c) is a view illustrating a pulse wave detected from the moving image.

The pulse wave detection device 1 arranges the pulse wave signal Qm output from each frame image in a time series (in the order of the frame images) and forms a pulse wave 35.

As described above, by specifying the skin portion of the user in each frame image, the pulse wave detection device 1 can detect a pulse wave while tracking/extracting the skin portion in accordance with movement of the user. As a result, the following features are obtained.

(Compatibility with Real-Time Processing)

In the prior-art technology, a moving image is taken while the subject is kept stationary in a state faced with the evaluation region 101. Since there is a possibility that the face goes out of the evaluation region 101 during photographing, the moving image after the photographing is analyzed.

On the other hand, since the pulse wave detection device 1 specifies the skin portion 26 in each frame image of the moving image, the evaluation region moves in the moving image as it is kept fixed to the skin of the user.

Since the skin portion does not go out of the evaluation region even if the face moves, the pulse wave can be detected on a real time basis.

Moreover, when the user's face is face recognized by each frame image and tracked, high computer processing capability is required, and a possibility of a failure of the face recognition is also high.

On the other hand, the pulse wave detection device 1 can track the skin portion with simple processing of specifying the skin portion by comparing the HSV image with the skin color data. Thus, it is suitable for the real-time processing.

Furthermore, since the pulse wave is detected by simple and low-load processing, drop of a frame (so-called drop frame) caused by the computer processing capability can be suppressed even in the real-time processing.

Since an interval between processed frame images is a measurement interval (sampling rate) of the pulse wave, widening of the measurement interval can be prevented by preventing the drop frame.

As a result, high time resolution of the pulse wave can be maintained, and detection accuracy of the pulse wave is improved.

Moreover, the face recognition processing is executed only at registration of the skin color data, and the skin color data already registered is used and thus, such a situation that the face recognition fails at a site and the skin color data cannot be sampled, which makes pulse detection impossible can be avoided, whereby measurement reliability is improved.

The pulse wave detection is mainly used in a case of monitoring a current physiological state of a target, and capability of real-time processing is important.

(Exclusion of Background)

In the prior-art technology, since it is difficult to match the evaluation region 101 with the shape of the subject's face, the disturbance element such as a background is included in the evaluation region 101, which might lower detection accuracy of the pulse wave.

On the other hand, in the pulse wave detection device 1, the evaluation region and the skin portion 26 match each other at all times and thus, inclusion of the disturbance element such as the background other than the face in the evaluation region can be prevented, whereby accurate pulse wave detection can be made.

(Exclusion of Face Portion not Relating to Pulse Wave)

In the prior-art technology, even when the subject's face is correctly set to the evaluation region 101, the face portions not relating to the pulse wave (hair, eye, mouth and the like) are included in the evaluation region and thus, it is likely that they affect the detection accuracy of pulse wave as the disturbance elements.

On the other hand, in the pulse wave detection device 1, since these face elements are excluded from the skin portion 26, the detection accuracy of the pulse wave can be improved.

Furthermore, even if the user blinks or opens/closes the mouth, since the skin portion 26 is dynamically set in accordance with the movement of the face, the disturbance elements by the face movement can be also excluded from the evaluation region.

Figure 4:
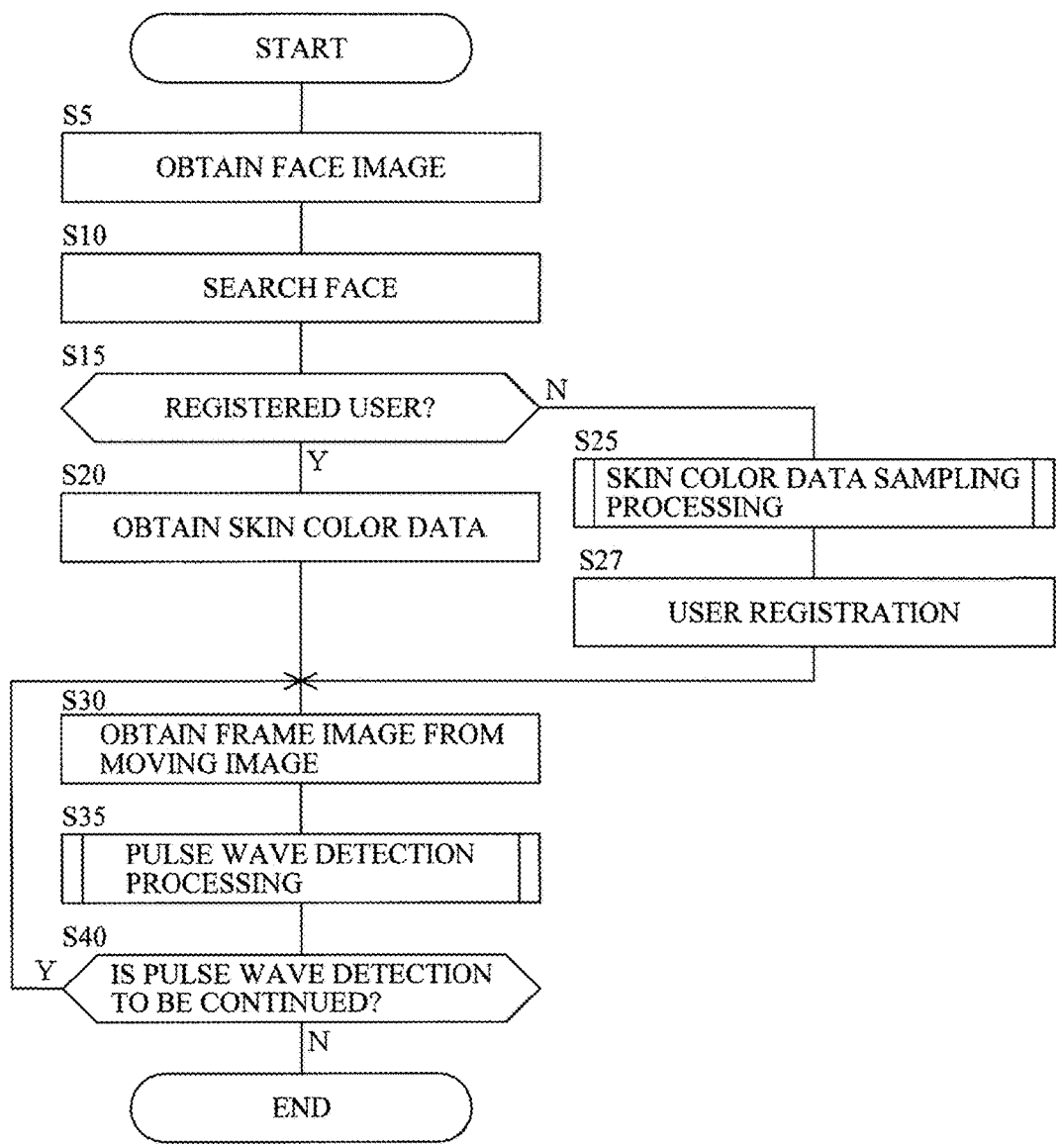
FIG. 4 is a flowchart for explaining a procedure of entire processing.

FIG. 4 is a flowchart for explaining a procedure of entire processing executed by the pulse wave detection device 1.

The following processing is executed by the CPU 2 in accordance with the pulse wave detection program 12.

First, when the CPU 2 detects that the user is seated at a designated position from a change in the image of the camera 8, it obtains an image of the user's face and stores it in the RAM 4 (Step 5).

This image may be taken as a still image or may be taken out of a frame image of the moving image.

As described above, the pulse wave detection device 1 includes moving image obtaining means for obtaining a moving image taking a region including at least the skin of the target, and the region including the skin includes the face of the target.

Subsequently, the CPU 2 face recognizes the image of the face stored in the RAM 4 and searches this by collating it with the face data in the user database 14 (Step 10).

When the face is searched, the CPU 2 determines that the user has been registered (Step 15; Y) and obtains the skin color data of the user from the user database 14 and stores it in the RAM 4 (Step 20).

On the other hand, when the face has not been searched, the CPU 2 determines that the user has not been registered yet (Step 15; N), executes the skin color data sampling processing and samples the skin color data from the image of the face (Step 25).

Then, the pulse wave detection device 1 generates face data from the image of the face and makes user registration by associating the face image with the skin color data and storing it in the user database 14 (Step 27).

When the CPU 2 obtains the skin color data, it obtains a frame image from the moving image transmitted from the camera 8 and stores it in the RAM 4 (Step 30).

Subsequently, the CPU 2 executes the pulse wave detection processing for processing a pulse wave from the frame image stored in the RAM 4 (Step 35).

Subsequently, the CPU 2 determines whether the pulse wave detection is to be continued or not (Step 40).

When the pulse wave detection is to be continued (Step 40; Y), the pulse wave detection device 1 returns to Step 30 and executes the pulse wave detection processing to the subsequent frame image in the moving image.

On the other hand, if the pulse wave detection is not to be continued since the user presses a stop button or the like (Step 40; N), the pulse wave detection device 1 finishes the processing.

Figure 5:
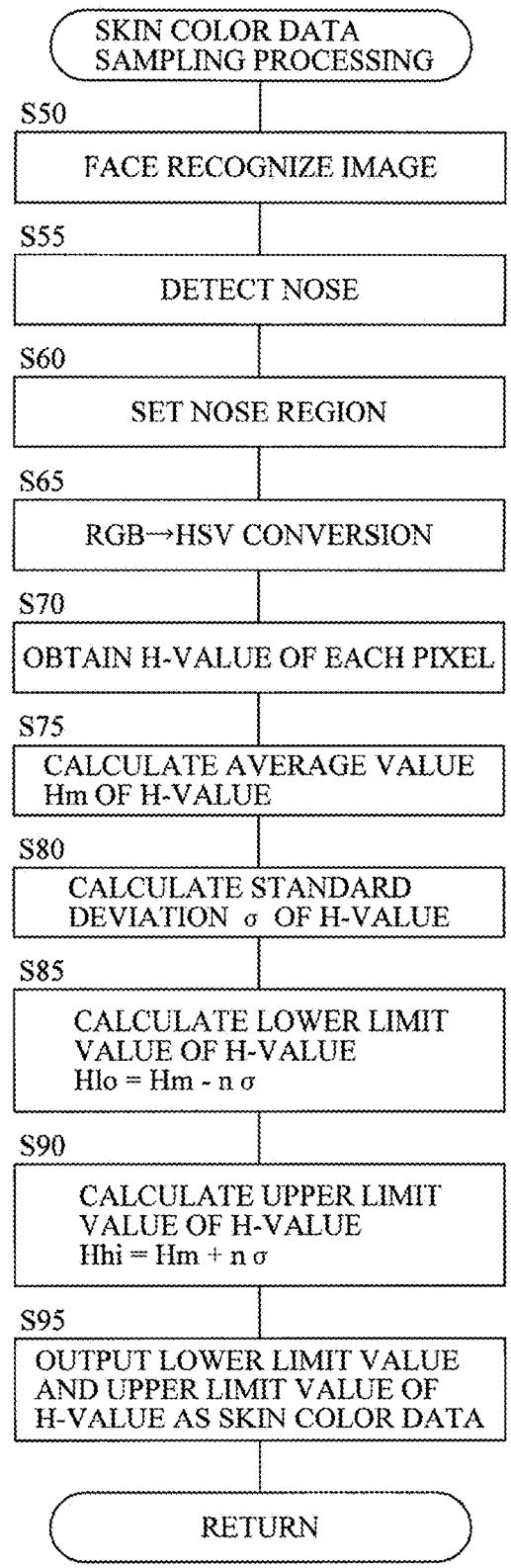
FIG. 5 is a flowchart for explaining a procedure of skin color data sampling processing.

FIG. 5 is a flowchart for explaining a procedure of the skin color data sampling processing at Step 25.

First, the CPU 2 reads out an image of the face from the RAM 4 and face recognizes it (Step 50) and then, detects the nose (Step 55).

Subsequently, the CPU 2 sets a nose region for sampling the skin color data sampling to the detected nose (Step 60).

As described above, the pulse wave detection device 1 includes face image obtaining means for obtaining an image taking the face of the target and region specifying means for specifying a predetermined region (nose region) where the face skin is exposed.

Subsequently, the CPU 2 color converts the color space of the nose region from the RGB space to the HSV space (Step 65) and obtains the H-value of each pixel (Step 70).

Subsequently, the CPU 2 calculates Hm by averaging the H-value of each pixel (Step 75) and moreover, calculates a standard deviation σ of the H-value (Step 80).

Subsequently, the CPU 2 calculates a lower limit value $Hlo = Hm - n \times \sigma$ of the H-value from Hm and σ and stores it in the RAM 4 (Step 85). Reference character n will be described later.

Furthermore, the CPU 2 calculates an upper limit value Hli=Hm+n×σ of the H-value from Hm and σ and stores it in the RAM 4 (Step 90).

Then, the CPU 2 outputs the lower limit value and the upper limit value of the H-value as the skin color data (Step 95) and returns to a main routine (FIG. 5).

The output skin color data (Hlo and Hhi) functions as a reference component which is a color space component to be a reference for specifying the skin portion of the target and is registered in the user registration at Step 27 (FIG. 4).

As described above, the pulse wave detection device 1 includes reference component registering means for registering a reference component and applies statistical processing by an average value and a standard deviation to the color space component of the nose region and makes registration.

Reference character n is a multiplier of σ and specifies a range of the H-value around Hm. As will be described later, the pulse wave detection device 1 specifies a portion where the H-value is within this range from the frame image as the skin portion and thus, reference character n can be adjusted to an appropriate value through experiments or the like.

By setting n=3, for example, a portion where the H-value is within a range of Hm±3σ is specified as the skin portion.

Figure 6:
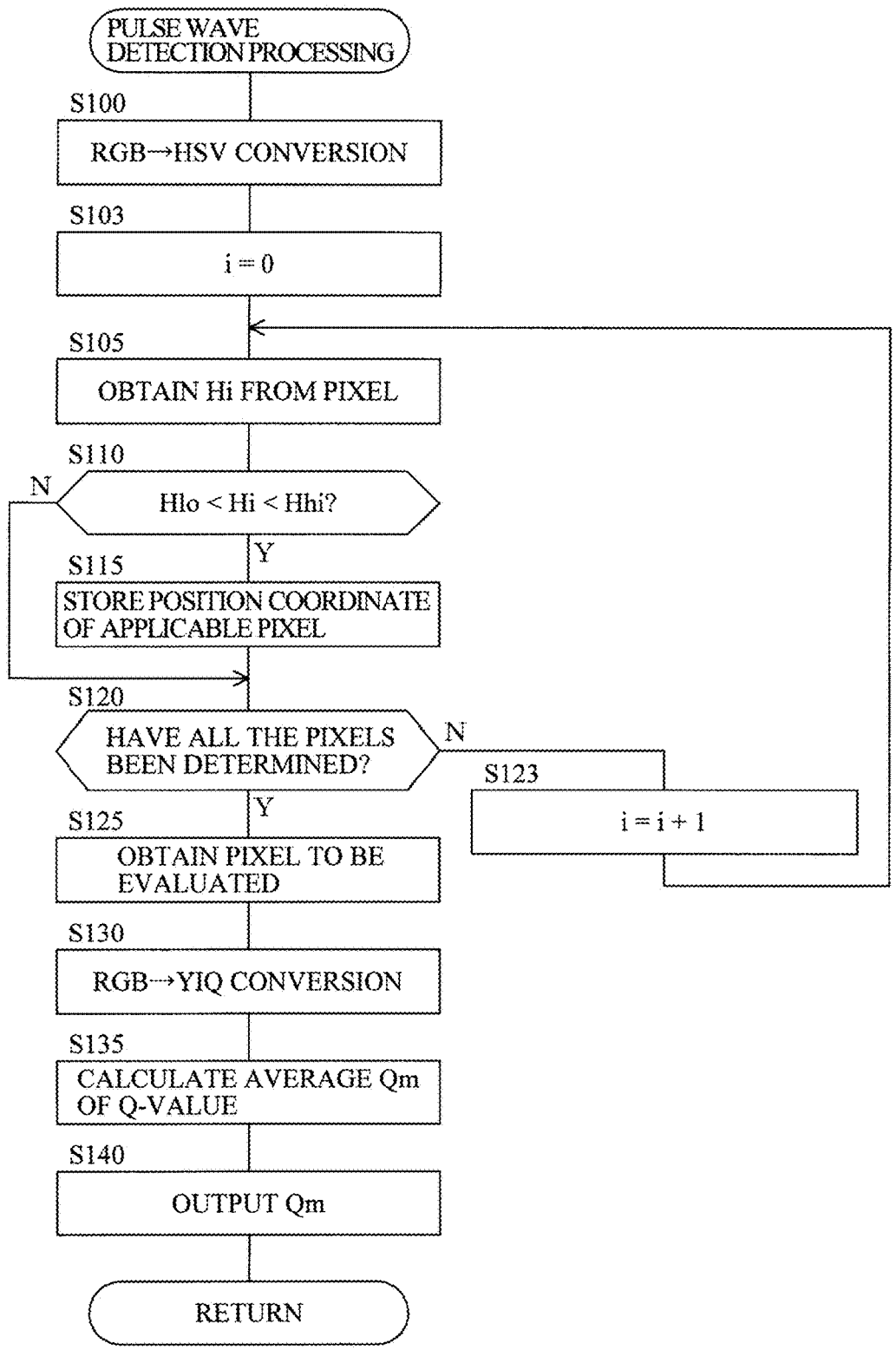
FIG. 6 is a flowchart for explaining a procedure of pulse wave detection processing.

FIG. 6 is a flowchart for explaining a procedure of the pulse wave detection processing at Step 35 (FIG. 5).

First, the CPU 2 coverts the color space of the frame image stored in the RAM 4 from the RGB space to the HSV space and stores the converted HSV image in the RAM 4 (Step 100).

Subsequently, the CPU 2 sets a counter i counting the order the pixel to i=0 (Step 103).

Subsequently, the CPU 2 obtains Hi which is the H-value of the i-th pixel in each pixel of the HSV image stored in the RAM 4 (Step 105).

Then, the CPU 2 determines whether Hi satisfies Hlo<Hi<Hhi or not, that is, whether Hi is within a range of the skin color data (Step 110).

When Hi is within this range, the CPU 2 determines that the pixel corresponds to the skin color data.

When Hi satisfies the inequality, that is, when Hi corresponds to the skin color data (Step 110; Y), the CPU 2 stores a position coordinate of the pixel in the RAM 4 (Step 115).

After the position coordinate is stored at Step 115 or when Hi is not within the range of the skin color data at Step 110 (Step 110: N), the CPU 2 determines whether the determination at Step 110 has been made for all the pixels in the HSV image or not (Step 120).

If there still is a pixel which has not determined yet (Step 120; N), the CPU 2 increments I by 1 and updates it to i=i+1 (Step 123), returns to Step 105 and repeats the similar processing to the subsequent pixel.

By executing Step 100 to Step 123 described above, the position coordinate of the pixel corresponding to the skin portion (pixel to be evaluated) is stored in the RAM 4.

Subsequently, the CPU 2 obtains the pixel to be evaluated in the frame image by specifying the pixel located at the position coordinate stored in the RAM 4 in the frame image (Step 125).

As described above, the pulse wave detection device 1 includes skin portion specifying means for specifying a skin portion of the target (pixel to be evaluated) shown on the moving image.

Moreover, this specification is made by taking the portion where the predetermined color space component in the moving image corresponds to the reference component as the skin portion by the pixel values.

Subsequently, the CPU 2 color converts the color space of the pixel to be evaluated from the RGB space to the YIQ space (Step 130).

Then, the CPU 2 calculates the average value Qm by averaging the Q-values of the pixels (Step 135), outputs it as the pulse wave signal (Step 140), and returns to the main routine (FIG. 4).

The pulse wave signal is superimposed on the Q-value of the pixel to be evaluated, and by averaging it to Qm, an influence of noise can be reduced.

By means of the processing described above, the pulse wave signal Qm is detected in one frame image, and by executing this to each of the continuing frame images and by arranging the pulse wave signals Qm in the order the frame images, a pulse wave illustrated in FIG. 3(*c*) is obtained by a temporal change of the pulse wave signal Qm.

As described above, the pulse wave detection device 1 includes pulse wave obtaining means for obtaining a pulse wave from the temporal change of the predetermined color space component in the skin portion and output means for outputting it.

As described above, the pulse wave detection device 1 carries out specification of the skin portion with the H component in the HSV space and the pulse wave detection with the Q component in the YIQ space.

Thus, the color space component used by skin portion specifying means for specifying the skin portion and the color space component used by the pulse wave obtaining means for obtaining the pulse wave are color space components different from each other.

Then, the pulse wave detection device 1 includes color space converting means for converting the color space of the moving image, and the skin portion specifying means and the pulse wave obtaining means obtain the color space component in the color space converted by the color space converting means.

Furthermore, the pulse wave detection device 1 can include monitoring means for monitoring a physical condition of the passenger of the transportation equipment by the pulse wave.

It is to be noted that, in this embodiment, after the skin portion is extracted from the frame image, the extracted skin portion is color converted from the RGB space to the YIQ space, but it may be so configured that the entire frame image is color converted to the YIQ space and then, the skin portion is extracted.

Second Embodiment

In the prior-art technology, pulse wave detection is made under the stable brightness by sunlight incident through the window of the laboratory.

On the other hand, when the pulse wave detection device 1 is to be used in a vehicle or at a medical site, photographing environments in use are varied, and particularly the brightness is expected to be changed during the pulse wave detection. Particularly when the pulse wave of a driver or a passenger is to be detected in the vehicle, a change in the brightness can frequently occur depending on a change in a running position or direction of the vehicle and a time slot.

Thus, whether or not a detection result is influenced by a brightness change caused when the pulse wave detection device 1 is actually used was examined. That is, the inventor of the present application changed the brightness by casting a shadow on the face of the subject using a round fan while the pulse wave was being detected under illumination by a fluorescent lamp.

FIG. 7 are a view illustrating a result by the experiment.

Figure 7A:
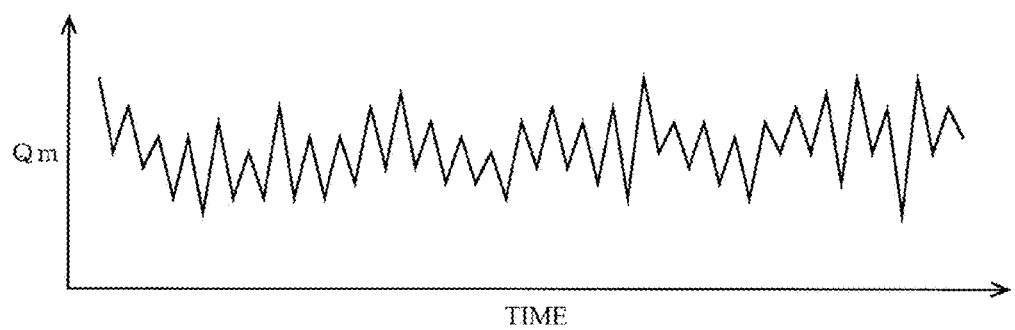
FIG. 7 are a view illustrating a result by an experiment.

FIG. 7(a) shows a temporal change of the pulse wave signal Qm when the brightness of the environment is not changed.

As illustrated in the figure, the pulse wave is clearly detected.

Figure 7B:
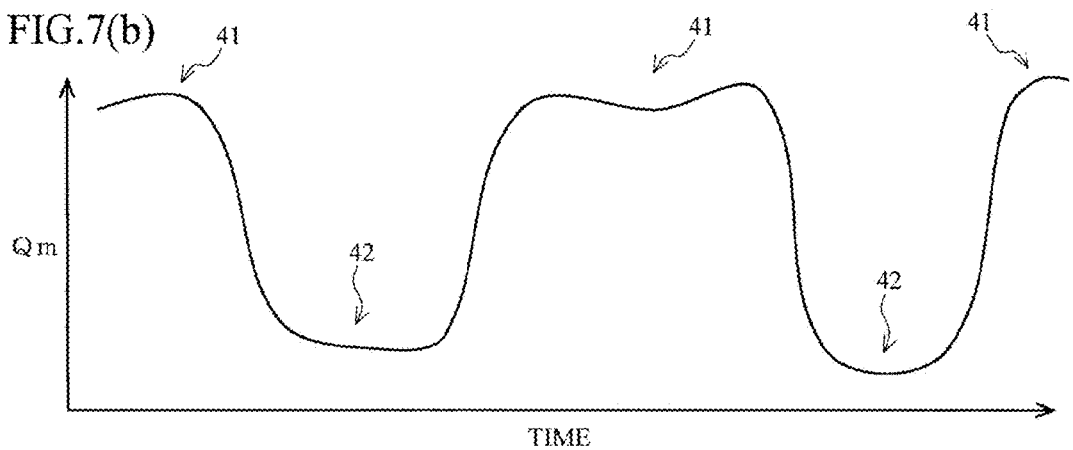

On the other hand, FIG. 7(b) shows a temporal change of the pulse wave signal Qm when only the brightness is changed by casting a shadow on the face of the subject by using a round fan.

A period 41 is a period without a shadow, while a period 42 is a period with a shadow.

As illustrated in the figure, the pulse wave signal Qm is largely changed by a change in the brightness, and a change in Qm is hidden in this change, which makes detection of the pulse wave difficult.

The inventor of the present application made a study on this problem and found that the pulse wave signal Qm does not appear in a portion of the eye (hereinafter, referred to as an eye portion).

Since the pulse wave signal Qm on which the brightness change is superimposed is detected from the skin portion and the brightness change (or intensity of the brightness) not including the pulse wave is detected from the eye portion, the brightness change can be corrected by subtracting the latter from the former.

Moreover, the inventor of the present application found that the Y component of the YIQ space is suitable for detection of the brightness change and in this embodiment, the brightness change is detected with the Y component.

Moreover, since the pulse wave signal Qm and the Y-value of the brightness belong to the same color space, it is only necessary to carry out subtraction.

Each figure in FIG. 8 is a view for explaining a correcting method of the brightness change.

Figure 8A:
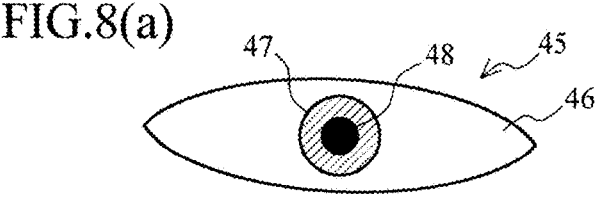
FIG. 8 are a view for explaining a correcting method of a change in brightness.

FIG. 8(a) is a view illustrating the eye portion 45 used for detection of the brightness change.

The eye portion 45 is constituted by a pupil portion 48 which is dark in color and located substantially at the center, an iris portion 47 around the pupil portion 48, and a white eye portion 46 which is close to white and located on an outer side of the iris portion 47.

The pulse wave detection device 1 sets a minimum value of the Q-value in the eye portion 45 to Qlo and a maximum value of the Q-value in the eye portion 45 to Qhi and registers them as eye color data.

It is to be noted that the pulse wave detection device 1 may set the Q-value of the white eye portion 46 to Qlo and the Q-value of the pupil portion 48 to Qhi and register them as the eye color data.

As will be described later, the pulse wave detection device 1 extracts the eye portion 45 from the eye region in the face of the user by using the eye color data and detects a change in brightness from a change in the Y-value of the extracted eye portion 45.

Figure 8B:
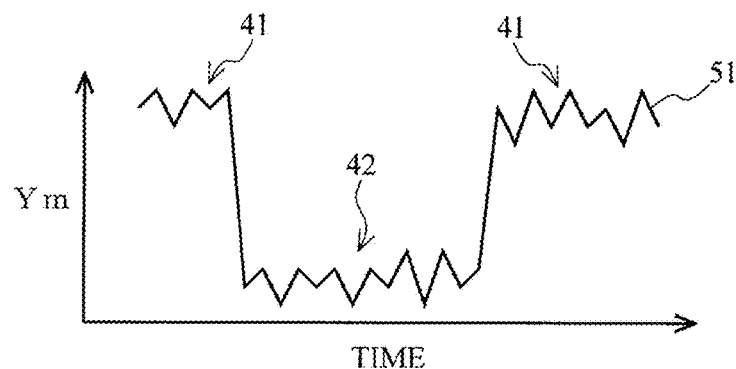

FIG. 8(b) is a view illustrating a brightness signal 51. The pulse wave detection device 1 averages the Y-value signal and generates Ym. By plotting this in a time series, the brightness signal 51 is obtained.

In the illustrated example, since the shadow was made on the face in the period 42, the brightness in the period 42 is smaller than that in the period 41.

Figure 8C:
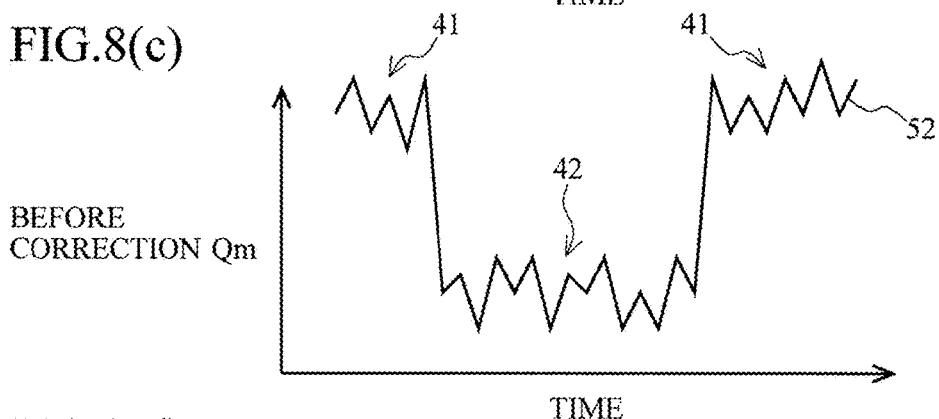

FIG. 8(c) is a view illustrating a before correction pulse wave signal 52.

The after correction pulse wave signal 52 is obtained by plotting the pulse wave signals Qm in a time series before the change in the brightness is corrected.

The pulse wave signal 52 before correction is subjected to an influence of the drop in brightness as illustrated in FIG. 8(c), and the pulse wave signal Qm in the period 42 also drops.

Figure 8D:
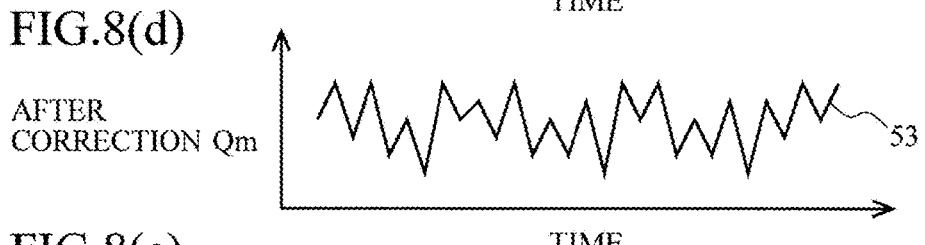

FIG. 8(d) is a view illustrating an after correction pulse wave signal 53.

The pulse wave detection device 1 generates the after correction pulse wave signal 53 by subtracting the brightness signal Ym from the pulse wave signal Qm before the correction. By plotting it in a time series, the after correction pulse wave signal 53 is obtained.

In the after correction pulse wave signal 53, since the influence by the change in the brightness has been removed, an appropriate pulse wave can be obtained even in the period 42 when the brightness drops.

Figure 8E:
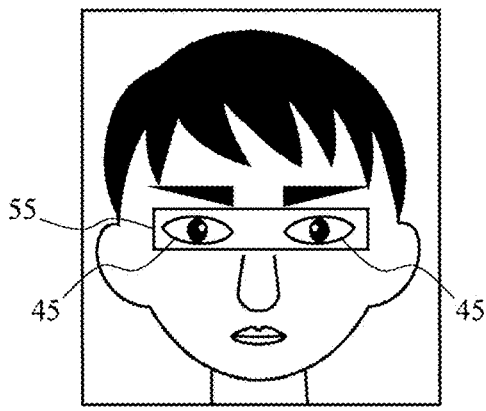
Figure 8F:
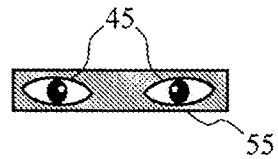

FIGS. 8(e) and 8(f) are views for explaining a method of specifying the eye portion 45 in the frame image in the moving image by the pulse wave detection device 1.

First, the pulse wave detection device 1 applies the face recognition processing to the frame image as illustrated in FIG. 8(e) and extracts the eye region 55 including the eye portion 45.

Then, the pulsed wave detection device 1 applies the eye color data to the eye region 55 and extracts the eye portion 45.

The eye portion 45 is extracted from the eye portion 55 as above because of the following reason.

If the eye color data is applied to the frame image, a portion accidentally corresponding to the eye color data such as a background can be extracted, for example, but since the eye region 55 is constituted by the skin portion and the eye portion 45, and the portion corresponding to the eye color data is only the eye portion 45 and thus, the eye portion 45 can be reliably specified.

Moreover, it is possible to directly specify the eye portion 45 by the face recognition, but accuracy of the face recognition needs to be improved, and a failure rate is also raised and thus, the eye region 55 is roughly specified in the image recognition as described above.

FIG. 9 is a flowchart for explaining a procedure of entire processing executed by the pulse wave detection device 1.

The same Steps as those in the first embodiment are given the same Step numbers, and the explanation will be simplified or omitted.

If the user is a registered user (Step 15; Y), the CPU 2 obtains the skin color data from the user database 14 (Step 20) and further obtains the eye color data (Step 150).

On the other hand, if the user is not a registered user (Step 15; N), the CPU 2 executes the skin color data sampling processing (Step 25) and further executes the eye color data sampling processing (Step 155) and registers the user by storing face data, skin color data, eye color data and the like in the user database 14 (Step 27).

The CPU 2 obtains the frame image (Step 30), executes the pulse wave detection processing (Step 35), and detects the pulse wave signal Qm before correction.

Subsequently, the CPU 2 executes the brightness change measure processing to the pulse wave signal Qm before correction (Step 160) and outputs the pulse wave signal Qm after correction.

FIG. 10 is a flowchart for explaining a procedure of the eye color data sampling processing at Step 155.

First, the CPU 2 face recognizes the image of the face used in the skin color data sampling processing (Step 180) and detects the eye portion (Step 185).

The pulse wave detection device 1 includes region specifying means for specifying the eye region in the face (the eye portion in this case) by the face recognition processing in the face image.

Subsequently, the CPU 2 specifies the eye portion to an evaluation region (Step 190) and converts the color spaces of all the pixels included in the eye portion from the RGB space to the YIQ space (Step 200).

Subsequently, the CPU 2 obtains the Q-value for each pixel included in the eye portion and stores it in the RAM 4 (Step 205).

Then, the CPU 2 sets a lowest value of the Q-value stored in the RAM 4 to Qlo (Step 210) and moreover, a highest value to Qhi (Step 215), makes them the eye color data and registers it in association with the face data and the skin color data of the user in the user database 14 (Step 220) and returns to the main routine (FIG. 9).

As described above, the pulse wave detection device 1 includes reference-component registering means for registering the color space components of the specified region as reference components (Qlo and Qhi) which become references for specifying the eye portion.

Then, the reference-component registering means registers a value to which statistical processing for specifying the minimum value and the maximum value to distribution of the color space components in the specified region.

FIG. 11 is a flowchart for explaining a procedure of the brightness change measure processing at Step 160.

First, the CPU 2 of the pulse wave detection device 1 detects the face by executing the face recognition in the frame image stored in the RAM 4 (Step 230) and moreover, detects the eye region (Step 235) and sets the detected eye region to the evaluation region (Step 240).

Subsequently, the CPU 2 converts the color space of the eye region from the RGB space to the YIQ space and stores it in the RAM 4 (Step 245).

Subsequently, the CPU 2 sets a counter j to 0 (Step 250) and obtains Qj which is the Q-value of a j-th pixel in the eye region from the RAM 4 (Step 253).

Then, the CPU 2 determines a size relationship among Qj, Qlo, and Qhi (Step 255).

In a case of Qlo<Qj<Qhi (Step 255; Y), the CPU 2 determines that the pixel is included in the eye portion and obtains the Y-value of the pixel and stores it in the RAM 4 (Step 260).

After the Y-value is obtained or if Qlo<Qj<Qhi is not satisfied (Step 255; N), the CPU 2 determines whether or not the determination has been made for all the pixels (Step 265).

If there still is a pixel which has not been determined yet (Step 265; N), the CPU 2 increments j by one and updates it to j=j+1 (Step 270) and then, returns to Step 253 and repeats the similar processing to the subsequent pixel.

By means of the processing described above, the Y-value of each pixel of the eye portion obtained by excluding the skin portion from the eye region is obtained.

As described above, the pulse wave detection device 1 includes eye portion specifying means for specifying the eye portion shown on the moving image by the pixel values by specifying a portion where the predetermined color space component corresponds to the registered reference component in the moving image as the eye portion.

After storing the Y-values of all the pixels as above in the RAM 4, the CPU 2 calculates an average value Ye by averaging them (Step 275).

The average value Ye corresponds to the brightness of a photographing environment and a difference from Ye in the frame images before and after that indicates a change in brightness.

Thus, by subtracting the average Ye of the respective brightness from each of the frame images, a change portion in the brightness can be corrected.

As described above, the pulse wave detection device 1 includes brightness change obtaining means for obtaining a change in brightness caused by a change in the photographing environment of the moving image from a change in the predetermined color space component of the eye portion.

Subsequently, the CPU 2 obtains the pulse wave signal Qm before correction (Step 276), obtains the pulse wave signal Qm after correction by subtracting the average value Ye from that (Step 277), outputs the calculated pulse wave signal Qm after correction (Step 278) and returns to the main routine (FIG. 9).

As described above, the pulse wave detection device 1 includes brightness correcting means for correcting brightness of the moving image by using a change in the brightness by the pixel values and pulse wave obtaining means for obtaining a pulse wave from a temporal change of the predetermined color space component in the corrected skin portion.

Moreover, the pulse wave detection device 1 obtains a change in the brightness with the Y component, specifies the skin portion with the H component and detects the pulse wave with the Q component and executes processing with different color components.

Then, the pulse wave detection device 1 includes color space converting means for converting these color spaces.

By means of the second embodiment described above, the following effects can be obtained.

(1) The pulse wave can be detected even when the brightness is changed by a change in the photographing environment such as change in light from outside, movement of the user or the like;

(2) The change in the brightness can be detected from the eye at the same time as the pulse wave is detected from the skin of the face; and (3) The change in brightness can be corrected even without a special device.

It is to be noted that, in this embodiment, the brightness of the skin portion is corrected after the skin portion is extracted from the frame image but the skin portion may be extracted after the brightness correction is applied to the entire frame image.

Third Embodiment

When the general-purpose camera 8 is used, for example, it is not known in a case where a human being appreciates a moving image, but there is fluctuation in characteristics in each pixel to such a degree that obstructs detection of the pulse wave.

In this embodiment, since the pulse wave is detected by the color component, it is affected by the fluctuation in chrominance (color quality) characteristics.

FIG. 12 are a view for explaining the fluctuation in chrominance by the camera characteristics.

Figure 12A:
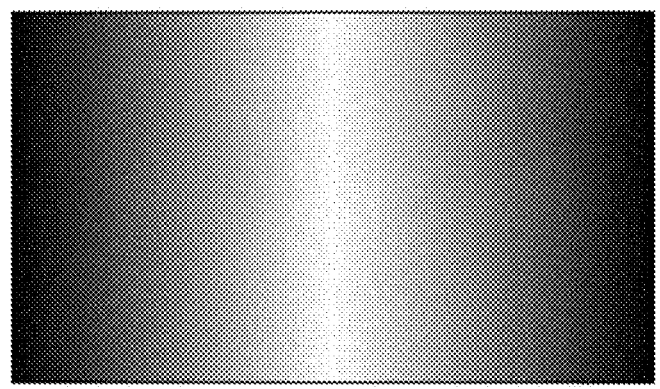
FIG. 12 are a view for variation in chrominance.

FIG. 12(a) is a view illustrating the fluctuation in the chrominance characteristics of the pixel in the camera 8 by contrast.

Since the chrominance characteristics are not uniform as above, if the user moves in the screen, a value of the chrominance is changed, which affects accuracy of pulse wave detection.

Figure 12B:
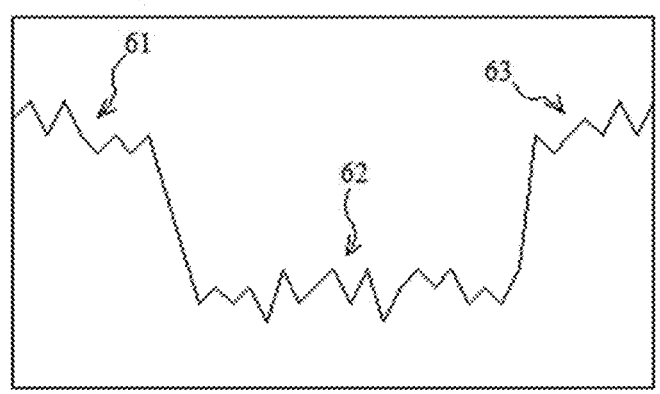

FIG. 12(b) is a view illustrating comparison of the detected pulse waves in a left region 61, a center region 62, and a right region 63 in the screen by having the subject move in the screen.

As illustrated in the figure, though the pulse waves at the same time should have been detected, a difference is caused in a height of the level by the difference in the chrominance.

Conventionally, the chrominance characteristics of the camera are corrected by an expert using a chart for calibration for various colors. This requires specialized knowledge and takes many processes, which is difficult for general uses.

Moreover, since correction is made for various colors, correction processing is complicated, and when the pulse wave is processed on the real time basis, drop of a frame occurs and it is likely that a rate relating to processing lowers.

Thus, in this embodiment, the color to be corrected is limited to the color of the user's face, and an average value of the chrominance for each pixel generated by movement of the user in the screen is stored as camera characteristic data.

By correcting a change in the chrominance by using the camera characteristic data, more accurate pulse wave can be detected.

Moreover, the movement of the user in the screen causes the skin portion to sweep the screen, but the pulse wave detection device 1 consecutively corrects the pixel in the region swept by the skin portion.

As described above in this embodiment, a correction value can be created automatically with movement of the user in the screen.

Figure 13:
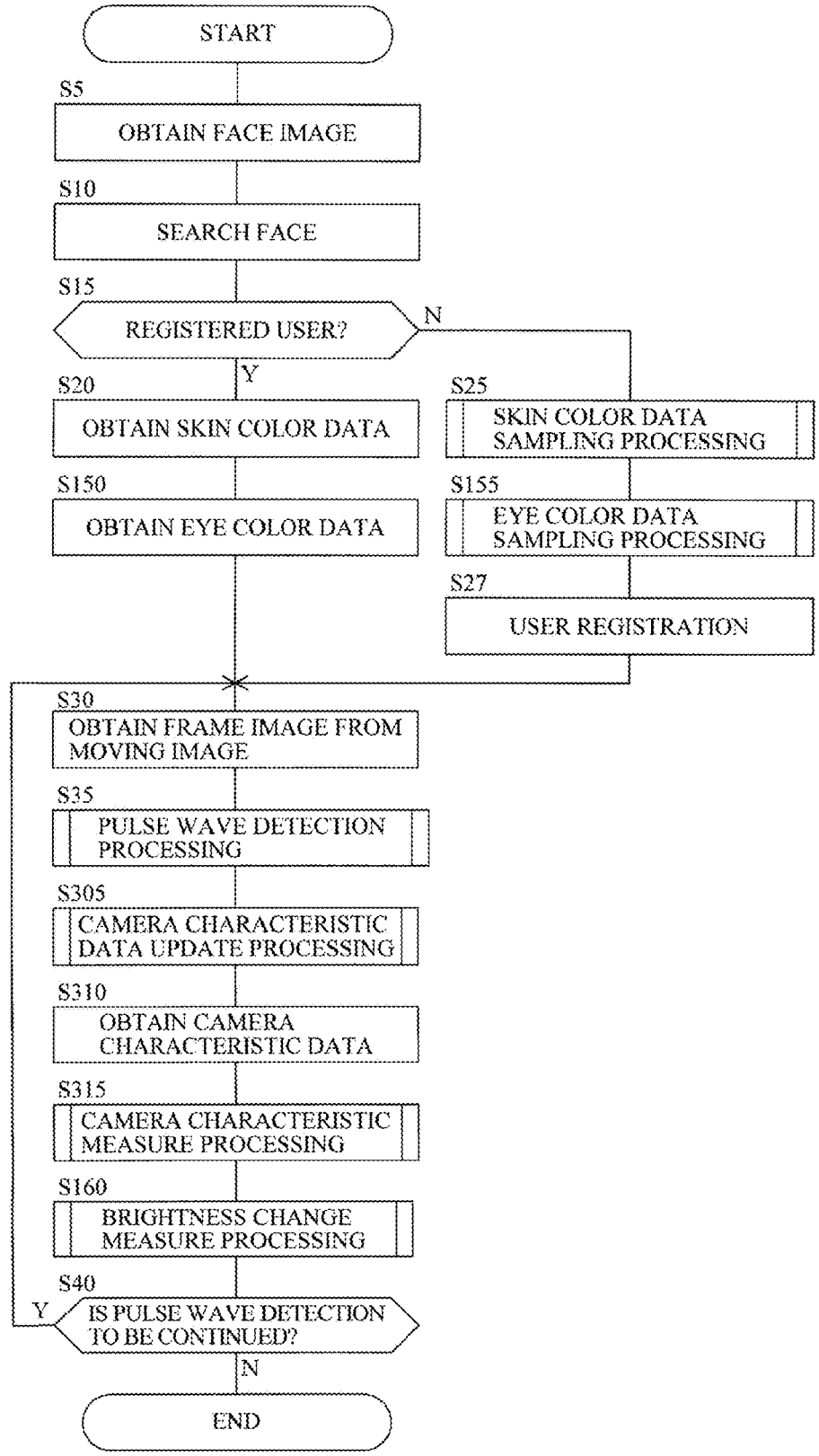
FIG. 13 is a flowchart for explaining a procedure of entire processing in a third embodiment.

FIG. 13 is a flowchart for explaining a procedure of entire processing executed by the pulse wave detection device 1.

The same Steps as those in the first embodiment and in the second embodiment are given the same Step numbers, and the explanation will be simplified or omitted.

After Step 5 to Step 30, the CPU 2 executes the pulse wave detection processing (Step 35) and then, executes camera characteristic update processing (Step 305).

Then, the CPU 2 obtains the updated latest camera characteristic data (Step 310) and applies correction by camera characteristic measure processing to the pulse wave signal Qm by using it (Step 315).

After that, the CPU 2 executes the brightness change measure processing to the pulse wave signal Qm to which the correction is applied by the camera characteristic (Step 160).

Figure 14:
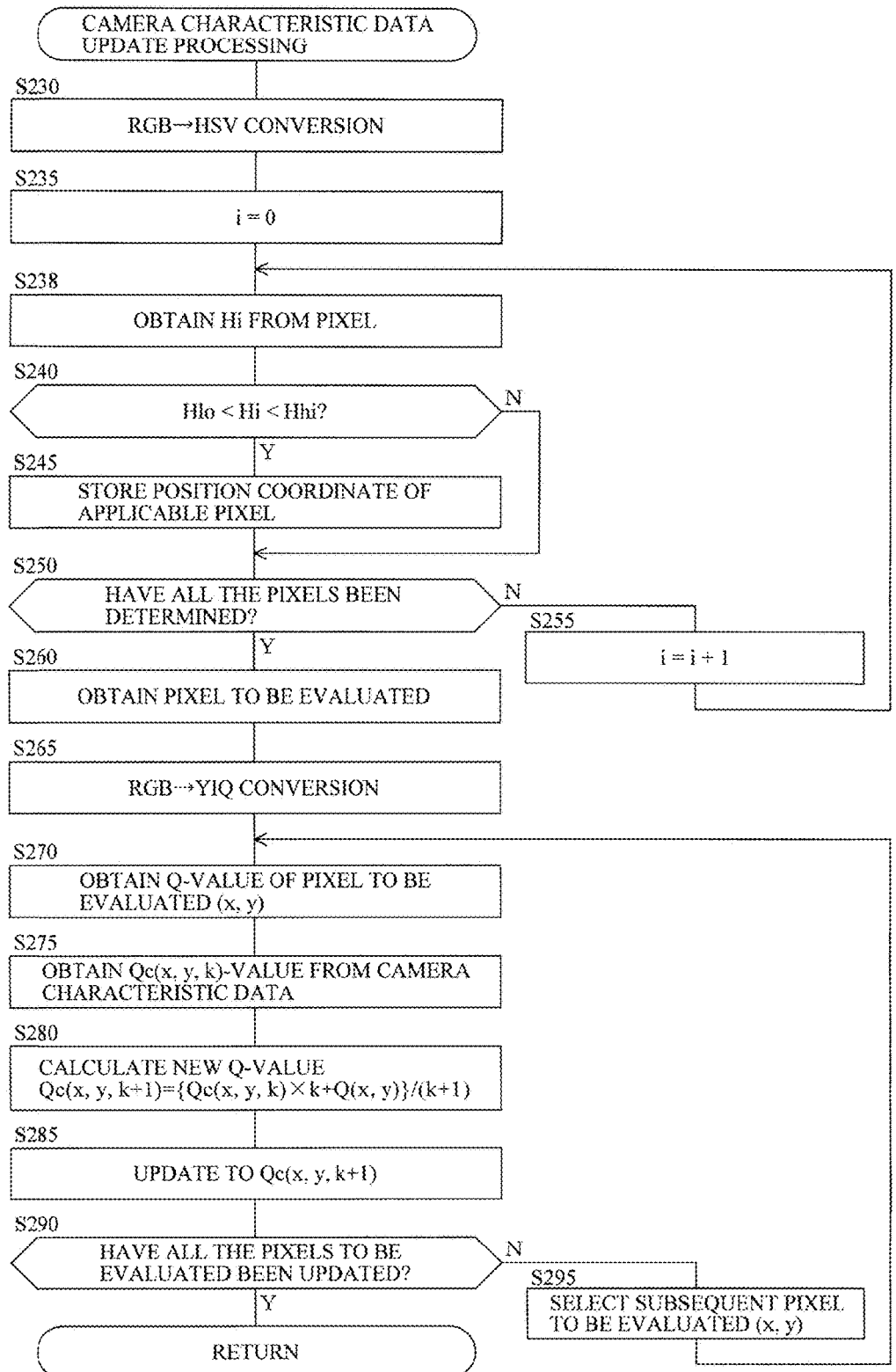
FIG. 14 is a flowchart for explaining a procedure of camera-characteristic data update processing.

FIG. 14 is a flowchart for explaining a procedure of the camera characteristic data update processing at Step 305 (FIG. 14).

Steps 230 to 265 are the same as Steps 100 to 130 in FIG. 6.

That is, the CPU 2 designates the pixel applicable to the skin portion in the frame image as a pixel to be evaluated and converts its color space from the RGB space to the YIQ space (Step 265).

Subsequently, the CPU 2 selects a pixel at a position coordinate (x, y) in the pixels to be evaluated (a selecting method may be an arbitrary algorithm), obtains the Q-value and stores it in the RAM 4 (Step 270).

Subsequently, the CPU 2 obtains the latest correction value (that is, the latest value until the previous correction) Qc(x, y, k) applicable to the position coordinate from the camera characteristic data 15 and stores it in the RAM 4 (Step 275).

Here, reference character k is a counter set for each pixel and is a parameter indicating a number of correction times of the pixel until the previous time.

Subsequently, the CPU 2 calculates a new Qc-value by the following equation by using these values stored in the RAM 4 and stores its result in the RAM 4 (Step 280).

$$Qc(x,y,k+1)=\{Qc(x,y,k)\times k+Q(x,y)\}/(k+1)$$

Subsequently, the CPU 2 updates Qc(x, y, k) of the camera characteristic data 15 with Qc(x, y, k+1) (Step 285).

As described above, the pulse wave detection device 1 includes update means for updating the correction value for each pixel by applying predetermined statistical processing to a change in the color space component generated on the skin portion with movement of the face in order to update the correction value for each pixel by using the statistical processing by the equation above.

Subsequently, the CPU 2 determines whether the Qc values have been updated for all the pixels to be evaluated or not (Step 290).

If there still is a pixel which has not been updated yet (Step 290; N), the CPU 2 selects the subsequent pixel to be evaluated (x, y) (Step 295) and then, returns to Step 270, and when update has been made for all the pixels (Step 290; Y), the CPU 2 finishes the update processing and returns to the main routine (FIG. 13).

Figure 15:
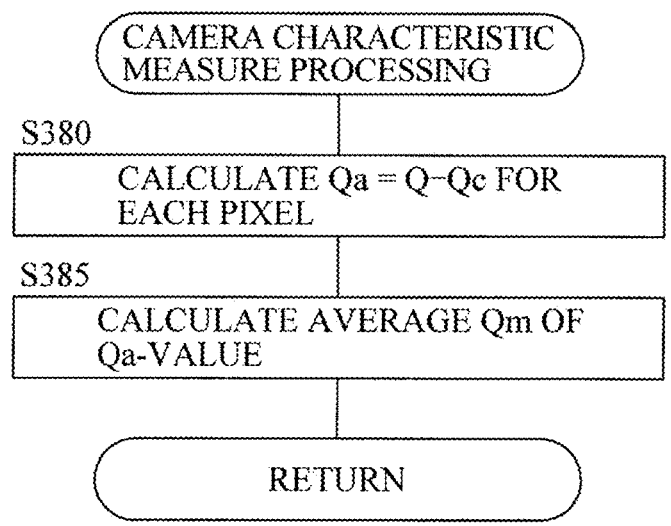
FIG. 15 is a flowchart for explaining a procedure of camera-characteristic measure processing.
Figure 16A:
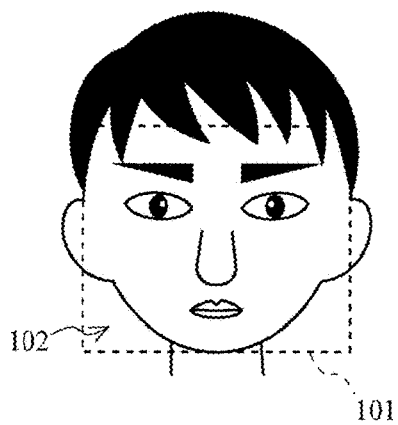
FIG. 16 are a view for explaining a prior-art technology.
Figure 16B:
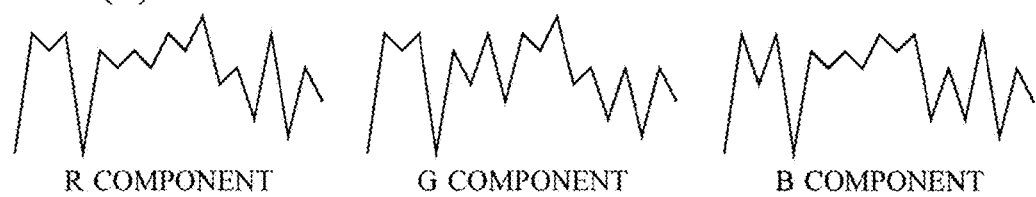

FIG. 15 is a flowchart for explaining a procedure of the camera characteristic measure processing at Step 315 (FIG. 13).

The CPU 2 calculates Qa (Q-value corrected by the camera characteristic measure) by subtracting Qc from the Q-value for each pixel set as the pixel to be evaluated in the frame image (Step 380), calculates an average value of Qa and sets it to the pulse wave signal Qm (Step 385) and returns to the main routine.

As described above, the pulse wave detection device 1 includes fluctuation correcting means for correcting fluctuation in the predetermined color space component generated in the moving image caused by the camera characteristics by using a correction value corresponding to the pixel for each pixel, pulse wave obtaining means for obtaining a pulse wave from a temporal change of the color space component in the corrected skin portion, and output means for outputting the pulse wave.

Furthermore, the pulse wave detection device 1 corrects the fluctuation by using the latest correction value while the correction value is updated and obtains the pulse wave from the skin portion corrected by the latest correction value by executing the camera characteristic data update processing at Step 305 (FIG. 13) and the camera characteristic measure processing at Step 315 (FIG. 13) in the same loop processing.

As described above, the pulse wave detection device 1 outputs the pulse wave signal Qm by using the latest correction value while correcting the camera characteristics.

Moreover, the camera characteristic measure processing can be configured to finish the correction when the correction value is converged to a certain degree.

In that case, correction is continued at least until the fluctuation by the camera characteristics becomes smaller than the fluctuation by the pulse wave signal.

As described above, the camera characteristic data 15 is completed and by subsequently using this characteristic, it is no longer necessary to execute the camera characteristic update processing in the pulse wave detection. As a result, a load of the CPU 2 is reduced, and that portion can be allocated to the other processing.

In this case, the pulse wave detection device 1 completes update of the correction value when the size of fluctuation in the color space components caused by the camera characteristics is converged to a value smaller than the size of the change in the color space components by the pulse wave.

According to the third embodiment, the following effects can be obtained.

(1) The camera characteristics can be detected and corrected while the pulse wave detection device 1 is in use. Thus, prior adjustment is not needed.

(2) Since the correction value is made with the movement of the user, it is suitable to be mounted on a vehicle and used for a passenger as a target, for example.

(3) Since the color to be corrected is limited to the color of the face, complicated calibration calculation is not needed, and drop of frame during moving image processing can be suppressed.

(4) As the result of suppression on the drop of a frame, time resolution of the pulse wave is improved. Thus, this is suitable for the real-time processing, and accuracy of pulse interval is also improved.

Subsequently, timing to start the processing by the pulse wave detection device 1 (FIGS. 4, 9, and 13) in the aforementioned first to third embodiments will be explained.

In each of the embodiments, the pulse wave detection processing by the pulse wave detection device 1 is started at anyone of the following timings. As each of the start timings, timing 1 may be set to default so that the user can change at arbitrary timing.

(1) Timing 1

The processing is started when the fact that the driver who is a monitoring target of the pulse wave is seated on a driver's seat is detected.

It is to be noted that, when a passenger other than the driver (a passenger on a seat next to the driver's seat or on a rear seat) is also a monitoring target of the pulse wave, the processing is started when the passenger is seated on any one of the seats to be targets.

In this case, regarding detection of the passenger, any one of cases where a load sensor is disposed on a seat to be a target (on a seat surface or a seat back portion) and a load at a threshold value or more is detected, where a seat belt is worn, or where an ignition key (for the driver's seat) is turned on, it is determined that the passenger is seated.

(2) Timing 2

A start button is disposed in the pulse wave detection devices 1, and when any one of the passengers selects the start button, the processing is started.

The start button in this case is constituted by the display unit 5 and the input unit 6. That is, the pulse wave detection device 1 displays an image of the start button on the display unit 5 and starts the processing when the touch panel of the input unit 6 detects a fact that the portion is touched.

Moreover, an independent hard switch may be provided as the input unit 6.

It is to be noted that the start button may be provided for each of the passengers to be monitored.

(3) Timing 3

When a door of the driver's seat of a vehicle on which the pulse wave detection device 1 is mounted is opened, the processing is started.

It is to be noted that, when the passenger other than the driver is also a monitoring target, the processing is started also when the door corresponding to the applicable passenger is opened.

The opening/closing of the door is detected by a known technology such as an opening/closing sensor (touch sensor) on a door portion or the like.

According to this timing 3, the monitoring of the pulse wave can be started as early as possible as compared with the other timings.

Particularly, since the processing before the pulse wave detection processing (Step 35) such as obtaining of the skin color data can be completed after the door is opened and until the passenger is seated, and the pulse wave can be detected for a longer time.

Subsequently, a usage method of the detected pulse wave will be explained. That is, by using the pulse wave detected by the pulse wave detection device 1 of this embodiment, a state of the driver including sleepiness, tensed state, awakened state such as fatigue and the like can be determined and coped with.

Technologies for detecting sleepiness of the driver from the pulse wave, for example, include a "sleepiness predicting device and sleepiness prediction system" in Japanese Patent No. JP2014-20678A. By using this technology as an example, presence of sleepiness can be monitored from the pulse wave of the driver.

In detail, by using the pulse wave detected by the pulse wave detection device 1, a pulse and HF of the driver are measured. The HF is a known index indicating a fluctuation amount of heartbeat intervals (fluctuation in a heart rate).

The sleepiness of the driver can be calculated by the following sleepiness numerical value Z.

$$Z = P \times 10 + (Q-1) \times 100$$

Reference character P denotes a drop amount of the pulse with respect to a value at a normal time (simply referred to as bpm), and reference character Q denotes an increase rate of the HF in a predetermined period (past 500 seconds, for example).

In a state with a sign of sleepiness, since sympathetic nervous system activities change from an enhanced state to a suppressed state, the pulse rate lowers. In a state where sleepiness occurs, since parasympathetic nervous system changes to the enhanced state, the pulse rate lowers, while the HF rises.

The pulse wave detection device 1 monitors the pulse wave, the pulse acquired from the pulse wave, the HF, the sleepiness numerical value z and the like and outputs vibration or sound when the sign of sleepiness is found or the sleepiness occurs, which can call an attention of the driver.

Moreover, since the pulse also changes in accordance with the tensed state, fatigue and the like in addition to the sleepiness, the pulse wave detection device 1 can also monitor the awakened state of the driver including these concepts by the pulse wave.

The three embodiments have been explained above, but according to the second embodiment, the following configuration can be obtained.

(1) 201-st Configuration

A pulse wave detection device comprising moving image obtaining means for obtaining a moving image photographing a region including a face of a target, eye portion specifying means for specifying an eye portion of the target shown on the moving image, brightness change obtaining means for obtaining a change in brightness caused by a change in a photographing environment of the moving image from a change in a predetermined color space component of the specified eye portion, brightness correcting means for correcting the brightness of the moving image using the obtained change in the brightness, pulse wave obtaining means for obtaining a pulse wave of the target from a temporal change in the predetermined color space component in a skin portion of the target corrected as above, and output means for outputting the obtained pulse wave.

(2) 202-nd Configuration

The pulse wave detection device of the 201-st configuration, further comprising skin portion specifying means for specifying a skin portion of the target shown on the obtained moving image, wherein the pulse wave obtaining means obtains a pulse wave of the target from the temporal change of the predetermined color space component on the specified skin portion.

(3) 203-rd Configuration

The pulse wave detection device of the 202-nd configuration, further comprising reference component registration means for registering a reference component which is a color space component to be a reference for specifying the eye portion of the target, wherein the eye portion specifying portion specifies a portion where the predetermined color space component corresponds to the registered reference component in the moving image as the eye portion.

(4) 204-th Configuration

The pulse wave detection device of the 202-nd or the 203-rd configuration, wherein the skin portion specifying means specifies a portion where the predetermined color space component corresponds to the registered reference component in the moving image as the skin portion.

(5) 205-th Configuration

The pulse wave detection device of the 202-nd, the 203-rd or the 204-th configuration, wherein the color space component used by the brightness change obtaining means for obtaining the change in brightness, the color space component used by the pulse wave obtaining means for obtaining the pulse wave, and the color space component used by the skin portion specifying means for specifying the skin portion are different color space components.

(6) 206-th Configuration

The pulse wave detection device of the 205-th configuration, wherein the color space component used by the brightness change obtaining means for obtaining the change in brightness and the color space component used by the pulse wave obtaining means for obtaining the pulse wave are a brightness component (Y) and a chromaticity component (Q) of a YIQ color space made of the brightness component (Y) and the chromaticity components (I, Q), respectively, and the color space component used by the skin portion specifying means for specifying the skin portion is a hue component (H) of an HSV color space made of the hue component (H), a saturation component (S), and a brightness component (V).

(7) 207-th configuration

The pulse wave detection device of any one of the 202-nd to the 206-th configurations, further comprising color space converting means for converting a color space, wherein the pulse wave obtaining means, the brightness change obtaining means, and the skin portion specifying means obtain a color space component in the color space obtained by converting the obtained moving image by the color space converting means.

(8) 208-th Configuration

The pulse wave detection device of the 203-rd configuration, further comprising face image obtaining means for obtaining a face image obtained by photographing the face of the target, and region specifying means for specifying a region of the eye in the face by face recognition processing in the obtained face image, wherein the reference component registration means registers a color space component in the specified region as the reference component.

(9) 209-th Configuration

The pulse wave detection device of the 208-th configuration, wherein the reference component registration means registers a value obtained by applying predetermined statistical processing to distribution of a color space component in the specified region as the reference component.

(10) 210-th Configuration

The pulse wave detection device of any one of the 201-st to the 207-th configurations, wherein the eye portion specifying means specifies the eye portion by the pixel values of the moving image.

(11) 211-th Configuration

The pulse wave detection device of any one of the 201-st to the 210-th configurations, wherein the brightness correcting means executes the correction by the pixel values of the moving image.

(12) 212-th Configuration

The pulse wave detection device of any one of the 201-st to the 211-th configurations, wherein the target is a passenger of transportation equipment, and monitoring means for monitoring a physical condition of the passenger by using the output pulse is provided.

(13) 213-th Configuration

A pulse wave detection program for realizing by a computer a moving image obtaining function of obtaining a moving image photographing a region including a face of a target, an eye portion specifying function of specifying an eye portion of the target shown on the moving image, a brightness change obtaining function of obtaining a change in brightness caused by a change in a photographing environment of the moving image from a change in a predetermined color space component of the specified eye portion, a brightness correcting function of correcting the brightness of the moving image using the obtained change in the brightness, a pulse wave obtaining function of obtaining a pulse wave of the target from a temporal change in the predetermined color space component in a skin portion of the target corrected as above, and an output function of outputting the obtained pulse wave.

By means of the configuration described above, the following effects can be obtained.

(1) According to the 201-st configuration, brightness of a moving image can be corrected by obtaining a change in the brightness from an eye portion of a target.

(2) According to the 202-nd configuration, the disturbance element shown on the moving image is excluded, only a skin portion is taken out, and a pulse wave can be detected therefrom and thus, accuracy of pulse wave detection can be improved.

(3) According to the 203-rd configuration, the disturbance element shown on the moving image is excluded, only the eye portion is taken out, and accuracy of brightness correction can be improved.

(4) According to the 204-th configuration, the skin portion can be easily extracted from the moving image by comparison with a reference component.

(5) According to the 205-th configuration, robustness against the disturbance element can be improved by employing combination of color space components suitable for an observation target (since targets to be observed by light are different in a change in brightness, skin, and a pulse wave).

(6) According to the 206-th configuration, by combining a Y-component found to be suitable for detection of the change in brightness, an H-component found to be suitable for specification of the skin portion, and a Q-component found to be suitable for pulse wave detection, robustness against the disturbance element can be further improved.

(7) According to the 207-th configuration, by including color space conversion processing inside a pulse wave detection device instead of an external device, the pulse wave can be detected easily on a real-time basis.

(8) According to the 208-th configuration, by sampling a reference value of an eye color from the target himself/herself, the reference value including a fine difference of the eye color in persons can be obtained easily.

(9) According to the 209-th configuration, biased distribution of eye colors with a large individual difference can be averaged by statistical processing, whereby reliability of a reference component can be improved.

(10) According to the 210-th configuration, since the eye portion is extracted for each pixel instead of a region surrounded by a closed curve (also pixels not applicable to the eye portion are scattered), the pixels acting as the disturbance element can be excluded from an evaluation target, whereby detection accuracy can be improved.

(11) According to the 211-th configuration, since the region surrounded by the closed curve can be corrected for each pixel instead of correction by a representative value, detection accuracy can be improved.

(12) According to the 212-th configuration, a physical condition of a passenger onboard transportation equipment can be monitored.

(13) According to the 213-th configuration, by distributing a pulse wave detection program and by installing this in a general-purpose computer, a pulse wave detection device can be configured easily and inexpensively.

Moreover, according to the third embodiment, the following configuration can be obtained.

(1) 301-st Configuration

A pulse wave detection device comprising moving image obtaining means for obtaining a moving image taking a region including at least skin of a target by a predetermined camera, skin portion specifying means for specifying a skin portion of the target shown on the obtained moving image, fluctuation correcting means for correcting fluctuation in predetermined color space components generated in the moving image caused by characteristics of the camera, pulse wave obtaining means for obtaining a pulse wave of the target from a temporal change of the color space components in the skin portion thus corrected, and output means for outputting the obtained pulse wave.

(2) 302-nd Configuration

The pulse wave detection device of the 301-st configuration characterized in that the region including at least the skin of the target includes the face of the target.

(3) 303-rd Configuration

The pulse wave detection device of the 302-nd configuration further comprising update means for updating a correction value used for the correction by applying predetermined statistical processing to a change in the color space components generated in the skin portion with movement of the face.

(4) 304-th configuration

The pulse wave detection device of the 303-rd configuration characterized in that the update means updates the correction value for each pixel constituting the moving image, and the fluctuation correcting means corrects the color space components by a correction value corresponding to the pixel for each of the pixels.

(5) 305-th Configuration

The pulse wave detection device of the 303-rd or the 304-th configuration characterized in that the update means completes the update when the size of fluctuation in the color space components caused by the camera characteristics converges to at least a value smaller than the size of a change in the color space components.

(6) 306-th Configuration

The pulse wave detection device of the 303-rd, the 304-th or the 305-th configuration characterized in that the fluctuation correcting means corrects the fluctuation by using the latest correction value while the update means updates the correction value, and the pulse wave obtaining means obtains the pulse wave from the skin portion corrected by the latest correction value.

(7) 307-th Configuration

The pulse wave detection device of any one of the 301-st to the 306-th configurations further comprising brightness change obtaining means for obtaining a change in brightness generated by a change in a photographing environment of the moving image, and brightness correcting means for correcting the brightness of the moving image by using the obtained change in the brightness, characterized in that the pulse wave obtaining means obtains a pulse wave of the target from a temporal change in the color space components in the skin portion further corrected by the brightness correcting means.

(8) 308-th Configuration

The pulse wave detection device of any one of the 301-st to the 307-th configurations characterized in that the color space component to be corrected by the fluctuation correcting means and the color space component used by the pulse wave obtaining means for obtaining the pulse wave are a chromaticity component (Q) of a YIQ color space made of a brightness component (Y) and chromaticity components (I, Q).

(9) 309-th Configuration

The pulse wave detection device of any one of the 301-st to the 308-th configurations characterized in that the target is a passenger of transportation equipment and monitoring means for monitoring a physical condition of the passenger by using the output pulse wave.

(10) 310-th Configuration

A pulse wave detection program for realizing by a computer a moving image obtaining function for obtaining a moving image taking a region including at least skin of a target by a predetermined camera, a skin portion specifying function for specifying a skin portion of the target shown on the obtained moving image, a fluctuation correcting function for correcting fluctuation in predetermined color space components generated in the moving image caused by characteristics of the camera, a pulse wave obtaining function for obtaining a pulse wave of the target from a temporal change of the color space components in the skin portion thus corrected, and an outputting function for outputting the obtained pulse wave.

By means of the configuration described above, the following effects can be obtained.

(1) According to the 301-st configuration, by correcting the fluctuation in the predetermined color space components generated in the moving image caused by the camera characteristics, the pulse wave can be favorably detected.

(2) According to the 302-nd configuration, the pulse wave can be detected from the face which can be photographed easily since the skin is usually exposed.

(3) According to the 303-rd configuration, the correction value is updated by a change in the color space component generated by movement of the face, and at that time, fluctuation in the correction value can be averaged by statistical processing.

(4) According to the 304-th configuration, by correcting the region not by a representative value but for each pixel, correction accuracy can be improved.

(5) According to the 305-th configuration, by converging the correction until the fluctuation in the color space components becomes smaller than the fluctuation in the pulse wave, the pulse wave can be detected favorably.

(6) According to the 306-th configuration, the pulse wave can be detected while correction is made.

(7) According to the 307-th configuration, by further correcting the brightness of the moving image, robustness against an environmental change is improved, and the pulse wave can be detected even in the brightness changes.

(8) According to the 308-th configuration, by setting the color space component for pulse wave detection to the Q component found to be suitable for the pulse wave detection, robustness against disturbance elements can be improved.

(9) According to the 309-th configuration, a physical condition of the passenger of transportation equipment can be monitored.

(10) According to the 310-th configuration, by distributing a pulse wave detection program and by installing it in a general-purpose computer, a pulse wave detection device can be configured easily and inexpensively.

Subsequently, a fourth embodiment will be explained.

In the aforementioned first embodiment, the case where, as an evaluation region for measuring a pulse wave, instead of a fixed region, a skin portion is specified by using the H (hue) component in the HSV components of each frame image in a moving image and set to an evaluation region (ROI), and Qm obtained by averaging the Q (chromaticity) values of the pixels in the YIQ components of the evaluation region is made a pulse wave signal of the frame image is explained.

On the other hand, in the fourth embodiment, when the evaluation region is to be determined, in addition to the H component, the S (saturation) component is used in order to specify the skin portion (evaluation region) with more accuracy.

FIG. 17 are a view for explaining a principle for specifying the skin portion by using the S component in the fourth embodiment.

Figure 17A:
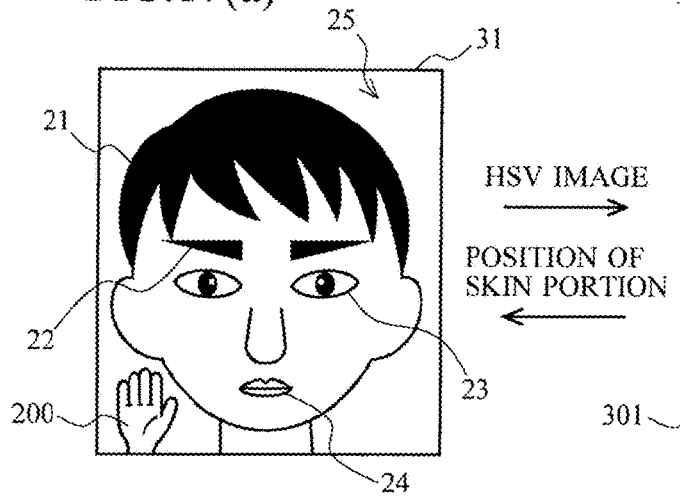
FIG. 17 are a principle explanatory view in a fourth embodiment.

FIG. 17(a) corresponds to the frame image 31 illustrated on the left side in FIG. 3(b) explained in the first embodiment.

Figure 17B:
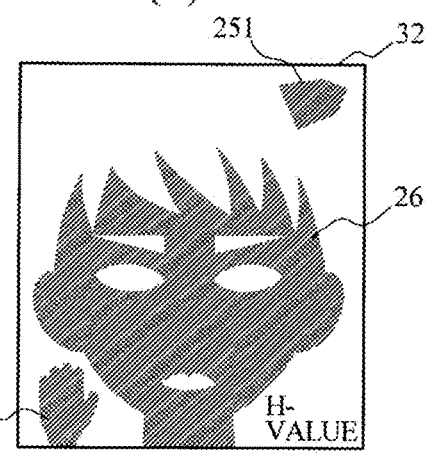

When this frame image 31 in FIG. 17(a) is color converted so as to generate the HSV image 32, and the skin portion 26 is specified from the H component in each pixel, the skin portion capable of measuring the pulse wave is explained in the view on the right side in FIG. 3(b) in the first embodiment, but actually, as illustrated in FIG. 17(b), other than the skin portion 26 in the face which should have been specified as the evaluation region, when disturbance 251 in the background is included or a hand 200 of a measurer is shown in the frame image 31, too, it is likely to be included in the evaluation region as the disturbance 301.

Thus, in this embodiment, in order to exclude this background or the portion other than the skin in the face (disturbances) from the evaluation region, adjustment processing using the S component is executed.

Figure 17C:
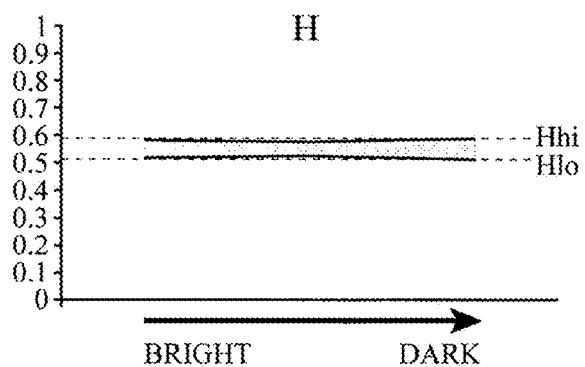

FIG. 17(c) illustrates a state of a change in the H component when brightness changes. A vertical axis in the figure is indicates a value obtained by normalizing each component.

As illustrated in FIG. 17(c), even if the brightness changes, a change in the H component of the skin portion is within a range from 0.5 to 0.6, and independence to the brightness change is high. In the present invention including this embodiment, the evaluation region is specified paying attention to the fact that independence of the H component in the skin portion is high.

Figure 17D:
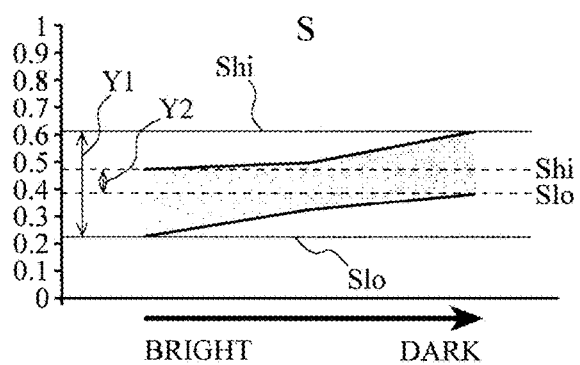

On the other hand, FIG. 17(d) illustrates a state of a change in the S component in the skin portion when brightness changes.

As illustrated in FIG. 17(d), the S component in the skin portion has a change range according to the brightness change larger than that of the H component, and independence of the S component to the brightness is low.

Thus, in this embodiment, by using optimal threshold values of the S component (Slo to Shi), the pixel to be disturbance is excluded from the evaluation region.

The optimal threshold values of the S component are determined by changing them within a range from a maximum range Y1 and a minimum range Y2 in FIG. 17(d).

Processing for detecting the pulse wave according to the fourth embodiment will be explained below.

The configuration of the pulse wave detection device 1 according to this embodiment is different from the first embodiment described in FIG. 1 in a point that, though the skin color data registered for each user of the user database 14 is Hlo and Hhi used as threshold values in the first embodiment, a lower limit value Slo and an upper limit value Shi used as threshold values are stored for further narrowing-down in the fourth embodiment. Since the other points are similar to the first embodiment, explanation will be omitted.

Moreover, a procedure of entire processing executed by the pulse wave detection device 1 of the fourth embodiment is the same as that in the first embodiment explained in FIG. 4.

Subsequently, skin color data sampling processing of this embodiment at Step 25 in FIG. 4 will be explained.

Figure 18:
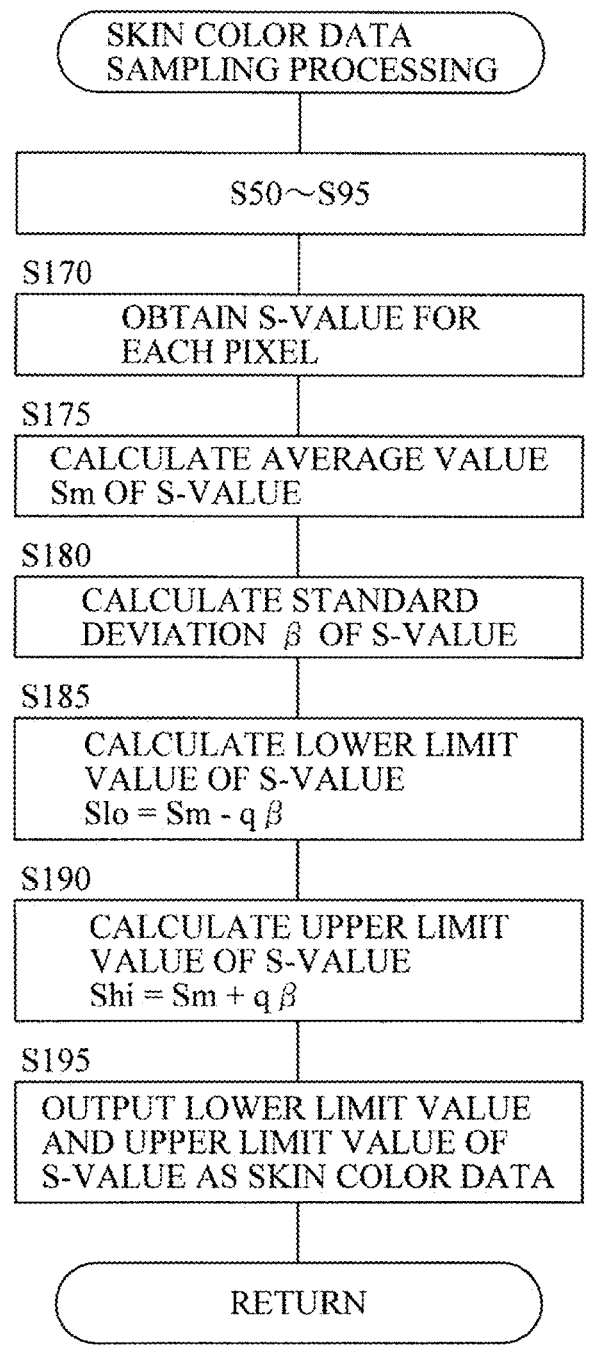
FIG. 18 is a flowchart of skin color data sampling processing in the fourth embodiment.

FIG. 18 is a flowchart of the skin color data sampling processing for processing skin color data from an image of the face.

In this skin color data sampling processing, the CPU 2 executes the same processing as Step 50 to Step 95 explained in FIG. 5 in the first embodiment so as to set the nose region and to output the lower limit value Hlo and the upper limit value Hhi of the H-value as skin data.

Then, the CPU 2 obtains the S value of each pixel (Step 170) in the nose region color converted to the HSV space at Step 65, calculates Sm by averaging the S value of each pixel (Step 175) and further calculates a standard deviation $\beta$ of the S value (Step 180).

Subsequently, the CPU 2 calculates the lower limit value Slo=Sm−q×$\beta$ of the S value from Sm and $\beta$ and stores it in the RAM 4 (Step 185). Reference numeral q will be described later.

Furthermore, the CPU 2 calculates the upper limit value Shi=Sm+q×$\beta$ of the S value and stores it in the RAM 4 (Step 190).

Then, the CPU 2 outputs the lower limit value and the upper limit value of the S value as the skin color data (Step 195) and returns to the main routine (FIG. 4).

The output skin color data (Slo and Shi) functions as a reference component which is a color space component to be a reference for specifying the skin portion of the target and is registered in user registration at Step 27.

As described above, the pulse wave detection device 1 includes reference component registering means for registering the reference component and applies the statistical processing by the average value and the standard deviation to the color space component of the nose region and registers it.

Here, q is a multiplier of β and specifies a range of the S-value around Sm. As will be described later, the pulse wave detection device 1 specifies a portion where the S-value is within this range from the frame image as the skin portion and thus, reference character q can be adjusted to an appropriate value through experiments or the like.

By setting q=3, for example, a portion where the S-value is within a range of Sm±3β is specified as the skin portion.

Subsequently, the pulse wave detection processing of this embodiment at Step 35 in FIG. 4 will be explained.

Figure 19:
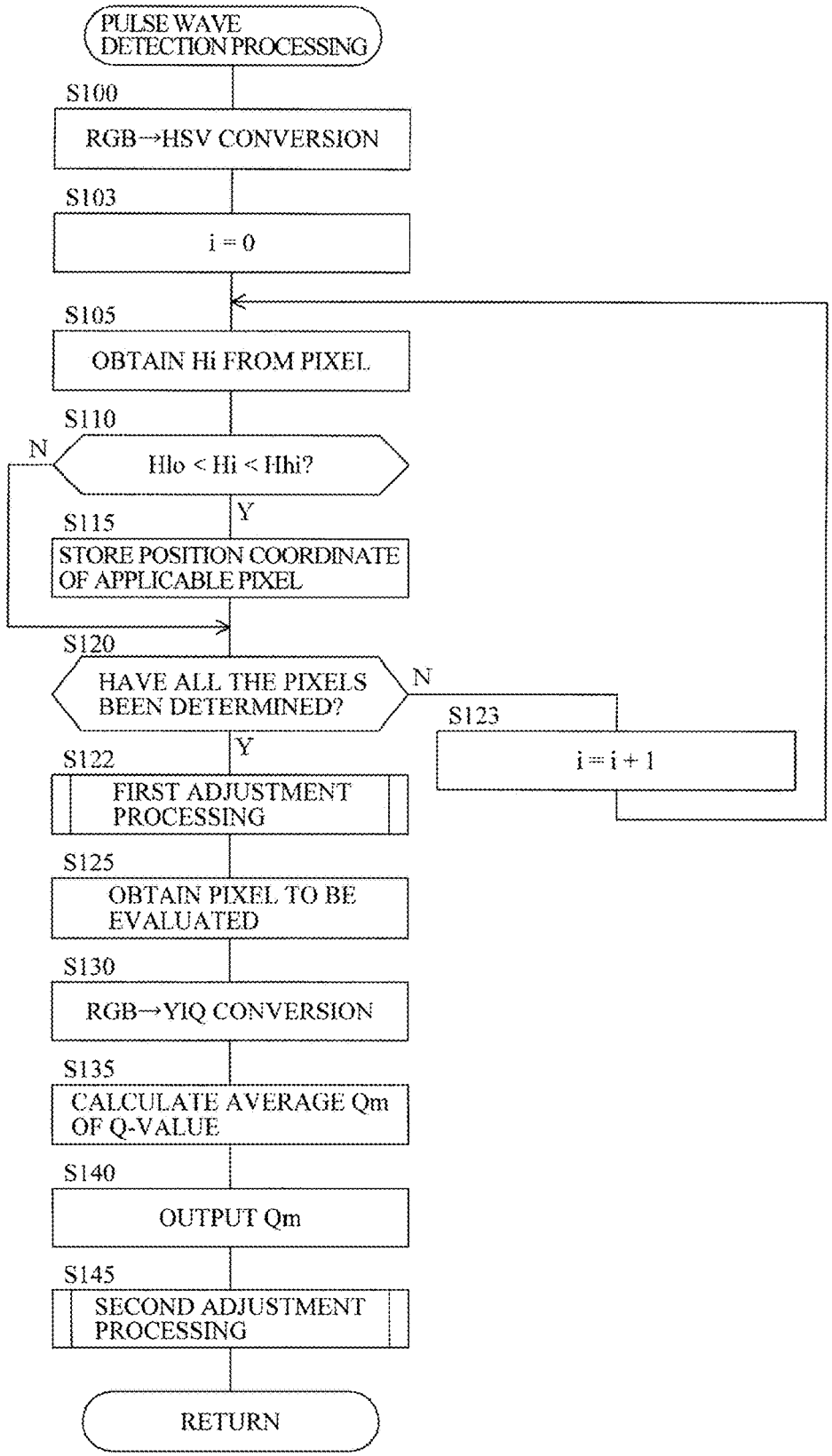
FIG. 19 is a flowchart of pulse wave detection processing in the fourth embodiment.

FIG. 19 is a flowchart of the pulse wave detection processing in the fourth embodiment.

FIG. 19 corresponds to the pulse wave detection processing in the first embodiment explained in FIG. 6, and the same Step numbers are given to the processing similar to FIG. 6, and the explanation will be omitted, and differences will be mainly explained.

That is, at Step 115 in the first embodiment, the position of the pixel satisfying the condition at Step 110 is stored as a pixel to be evaluated (Step 115), but at Step 115 in the fourth embodiment, the CPU 2 stores a position coordinate of the pixel satisfying the condition at Step 119 in the RAM 4 not as the pixel to be evaluated but as a candidate pixel.

Then, after determination on whether it is a candidate image or not is made for all the pixels in 1 frame image (Step 120; Y), the CPU 2 executes first adjustment processing on the basis of the S component (Step 122) and determines the evaluation target image.

Moreover, the CPU 2 executes second adjustment processing by using the S component to Qm of a predetermined plurality of frame images (Step 145).

Details of the first adjustment processing and the second adjustment processing will be described later.

Here, the principle of the first adjustment processing will be explained by referring to FIGS. 20 to 22.

FIG. 20 are a principle explanatory view of the first adjustment processing when a measurement region is narrow, FIG. 21 are a principle explanatory view of the first adjustment processing when there are many disturbances, and FIG. 22 are an explanatory view on an adjustment range in the first adjustment processing.

In the first adjustment processing, a pixel within Hlo to Hhi stored as the skin color data is specified as a candidate pixel and it is further narrowed down by Slo to Shi. Views on upper sides in FIGS. 20 and 21 illustrate all the narrowed-down pixels after the narrowing-down.

Then, in all the pixels after the narrowing-down, face regions 26a and 26c which are skin portions of the face are specified (estimated). This specification of the face regions is made such that, for example, a center part (a center point of the frame image, for example) of the face image which should be present in the frame image is specified in advance, and a collection of pixels including this center part (a collection of adjacent pixels) is taken as a face region. Alternatively, when a specific person in the vehicle or a driver is to be taken as a person to be measured, for example, a largest collection of the pixels in all the narrowed-down pixels may be specified (estimated) as the face region.

As illustrated in FIG. 20(*a*), when the number of pixels of this face region is smaller than a threshold value P2 specified in advance, amplitude of raw signals continuously recording the average Qm acquired for each frame image is small (figure on a lower side), and the pulse wave cannot be measured accurately. That is considered to be because the range between Slo and Shi by the skin color data used in the narrowing-down is too small and the narrowing-down is excessive.

Thus, as illustrated in the figure at the center in FIG. 20(*b*), narrowing-down is performed by acquiring a range from Slo to Shi with the number of pixels in the face region at the threshold value P2. That is, the range between Slo and Shi is gradually widened from the range by the skin color data so as to determine the range with the number of pixels in the face region at P2.

It is to be noted that, by widening the range between Slo and Shi, as illustrated in the figure on the upper side in FIG. 20(*b*), the pixels in the face region 26b included in the narrowed-down pixels increase, and measurement of the pulse wave is made possible.

By widening the range between Slo and Shi, pixels of disturbances 252b and 253b also increase, but since the number of disturbance pixels on the increase is not so many, an influence by the increase in the disturbance is small.

On the other hand, when the pixel other than the face region in all the narrowed-down pixels is taken as disturbance, as illustrated at the center in FIG. 21(*a*), when the number of pixels of disturbance is larger than a threshold value P1 specified in advance, disturbance signals are superimposed on raw signals continuously recording the average value Qm as illustrated in the lower figure and thus, the pulse wave can no longer be measured. That is considered to be because the range between Slo and Shi by the skin color data becomes too wide and many disturbances are included.

Thus, as illustrated in the figure at the center in FIG. 21(*b*) the range between Slo and Shi where the number of pixels of disturbance is P1 is acquired by narrowing-down. That is, by gradually narrowing down the range between Slo and Shi from the range by the skin color data, a range where the number of pixels of disturbance is P1 is determined.

By narrowing down the range between Slo and Shi, the pixels of disturbances 252d and 253d included in the narrowed-down pixels decrease as illustrated in the upper figure in FIG. 21(*b*), and the continuously recorded raw signals begin to indicate the pulse wave.

It is to be noted that, by narrowing down the range between Slo and Shi, the pixels in a face region 26d also decrease, but since the value of Qm is an average value, it is not a problem.

It is to be noted that, for the threshold value P2 for the number of pixels in the face region and the threshold value P1 for the number of pixels of disturbance, optimal values are determined in advance on the basis of a size of the frame image or an assumed distance from the camera to the face.

In a case where the driver in the vehicle is a target to be measured, and the size of the frame image is 480×640 pixels, for example, they are set as P1=1000 and P2=71000.

Subsequently, an adjustment range in the first adjustment processing will be explained.

FIG. 22(*a*) illustrates an adjustment state when the range between Slo and Shi stored in the skin color data in the user database 14 is narrow. As illustrated in this figure, when the range of the skin color data is narrow (Slo is 0.3 and Shi is 0.35), as explained in FIG. 20, the number of pixels in the face region becomes small. Thus, by decreasing Slo and increasing Shi, the range between Slo and Shi is widened, and the number of pixels in the face region is acquired again with the widened value. If this number of pixels is less than P2, the range between Slo and Shi is further widened and repeated until the number of pixels in the face region reaches P2 or more.

Figure 22A:
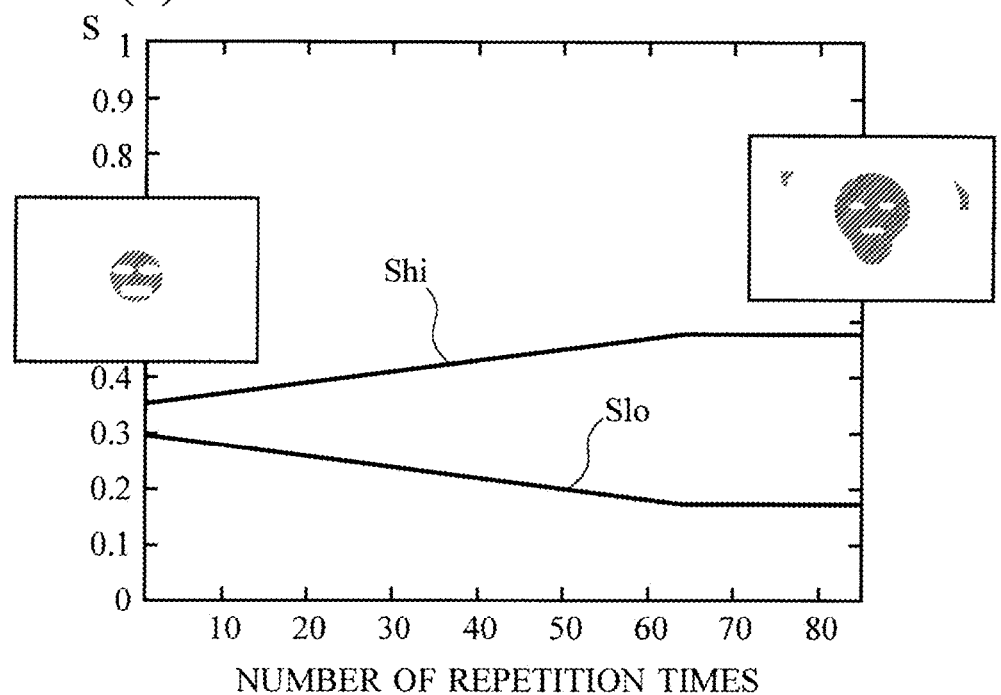
FIG. 22 are an explanatory view for an adjustment range in the first adjustment processing.

On the left vertical axis in FIG. 22(a), the narrowed-down pixel in FIG. 20(a) before the first adjustment processing is illustrated, while on the right vertical axis, the narrowed-down pixel in FIG. 20(b) after the first adjustment processing is illustrated.

Figure 22B:
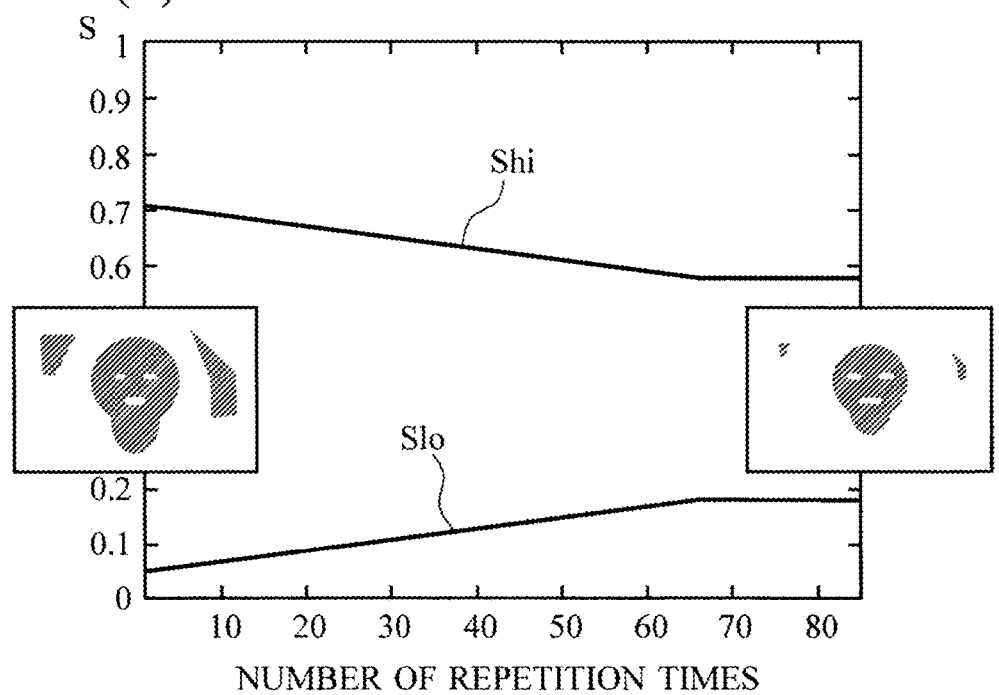

FIG. 22(b) illustrates the adjustment state when the range between Slo and Shi of the skin color data is wide.

As illustrated in FIG. 22(b), when the range of the skin color data is wide (Slo is 0.05, and Shi is 0.71), as explained in FIG. 21, the disturbance other than the face region increases. Thus, by increasing Slo and decreasing Shi, the range between Slo and Shi is narrowed, and the number of pixels of disturbance is acquired again with the narrowed-down value. If this number of pixels is larger than P1, the range between Slo and Shi is further narrowed down and repeated until the number of pixels of disturbance reaches P1.

On the left vertical axis in FIG. 22(b), the narrowed-down pixel in FIG. 21(a) before the first adjustment processing is illustrated, while on the right vertical axis, the narrowed-down pixel in FIG. 21(b) after the first adjustment processing is illustrated.

It is to be noted that, the lateral axis illustrated in FIG. 22 indicates the number of repetition times, and repetition is made until the number of pixels in the face region reaches P2 or more and the number of pixels of disturbance reaches P1 or less, and repetition is made at the maximum to a predetermined number of times (65 times in the example in FIG. 22). This number of repetition times can be changed.

It is to be noted that, in this embodiment, it is set such that the range is changed by 0.004 each at every repetition by increasing/decreasing with a range of 0.002, but this increase/decrease range is also arbitrary. In order to decrease a load at the same time when the processing is to be quickened, for example, the range is increased, while the range may be narrowed in the opposite case.

Subsequently, a detailed operation of the first adjustment processing (Step 122) in FIG. 19 will be explained.

Figure 23:
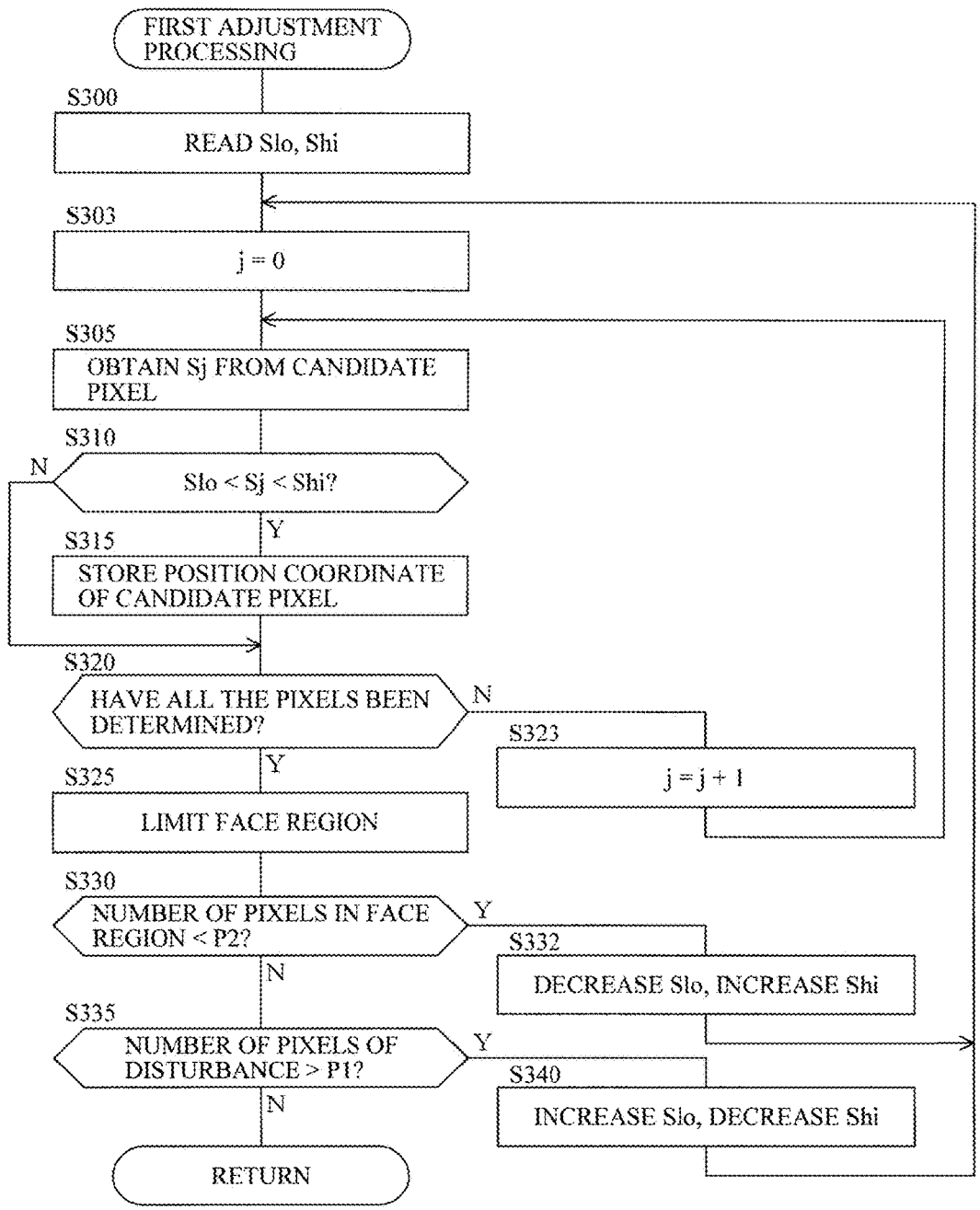
FIG. 23 is a flowchart of the first adjustment processing.

FIG. 23 is a flowchart of the first adjustment processing.

First, the CPU 2 reads the skin color data Slo and Shi from the user database 14 and stores them as initial values of the S component in the RAM 4 (Step 300).

Subsequently, the CPU 2 sets a counter j for counting the order of the pixels to j=0 (Step 303).

Subsequently, the CPU 2 obtains Sj which is the S-value of the j-th pixel in the pixels in the HSV image stored in the RAM 4 (Step 305). Regarding each of the pixels obtained here, each candidate pixel stored in the RAM 4 at Step 115 (FIG. 19) in this embodiment is a target of Sj, and the HSV pixel corresponding to the position coordinate of the applicable candidate pixel Sj stored in the RAM 4 is obtained among the HSV pixels converted at Step 100.

Then, the CPU 2 determines whether the candidate pixel Sj satisfies Slo<Sj<Shi or not, that is, whether Sj is within the range of skin color data or not (Step 310).

If the candidate pixel Sj is within this range between Slo and Shi (Step 310; Y), the CPU 2 sets the applicable pixel Sj to a narrowed-down pixel and stores its position coordinate in the RAM 4 (Step 315).

After the position coordinate of the narrowed-down pixel is stored at Step 315, or if the candidate pixel Sj is not within the range Slo to Shi (Step 310; N), the CPU 2 determines whether the determination at Step 310 has been made for all the candidate pixels (Step 320).

If there still is a candidate pixel which has not been determined yet (Step 320; N), the CPU 2 increments j by one and updates it to j=j+1 (Step 323), returns to Step 305 and repeats the similar processing to the subsequent candidate pixel.

By executing Step 303 to Step 323 above, the position coordinate of the pixel (narrowed-down pixel) corresponding to the skin portion is stored in the RAM 4.

Subsequently, the CPU 2 limits the face region from all the narrowed-down pixels (Step 325).

That is, the CPU 2 specifies a pixel collection of the narrowed-down pixels from all the narrowed-down pixels as targets. For example, in the case of the narrowed-down pixel illustrated in the upper figure in FIG. 21(a), the pixel collections 26c, 252c, and 253c are specified.

Then, in the pixel collections 26c, 252c, and 253c, the pixel collection 26c including the center part (specified in advance as a center point of the frame image, for example) in the face image which should be present in the frame image is taken as a face region as described above.

Subsequently, the CPU 2 counts the number of pixels in the limited face region and determines whether the counted number of pixels is less than the threshold value P2 or not (Step 330).

If the number of pixels in the face region is less than P2 (Step 330; Y), as explained in FIG. 20(a), the pulse wave can no longer be taken out of the continued raw signals of Qm due to excessive narrowing, and thus, the CPU 2 decreases Slo and increases Shi stored in the RAM 4 at Step 300 so as to widen the narrowing-down range by the S component (Step 332).

After that, the CPU 2 returns to Step 303 and performs narrowing-down by the S component after the change again for all the candidate images Sj in the same frame image (Step 303 to Step 323), limits the face region from the narrowed-down candidate image again (Step 325), and repeats it until the number of pixels in the face region reaches P2 or more by narrowing-down again.

If the number of pixels in the face region is P2 or more (Step 330; N), the CPU 2 counts the number of pixels of disturbance (pixels other than the face region) and determines whether the counted number of pixels is larger than the threshold value P1 or not (Step 335).

If the number of pixels of disturbance is larger than P1 (Step 335; Y), as explained in FIG. 21(a), the disturbance component is included in the continued Qm raw signals too much, and thus, the CPU 2 increases Slo and decreases Shi stored in the RAM 4 at Step 300 so as to narrow the narrowing-down range by the S component (Step 340).

After that, the CPU 2 returns to Step 303 and performs narrowing-down by the S component after the change again for all the candidate images Sj in the same frame image (Step 303 to Step 323), limits the face region from the narrowed-down candidate image again (Step 325), and repeats it until the number of disturbance reaches P1 or less by narrowing-down again.

If the number of pixels of disturbance is P1 or less (Step 335; N), the CPU 2 finishes the first adjustment processing and returns to the main routine.

When the first adjustment processing is finished, the CPU 2 proceeds to Step 125 in FIG. 19 and continues the processing.

That is, the CPU 2 specifies the pixel of the frame image (pixel converted to HSV at Step 100) located at the position coordinate of the narrowed-down pixel stored in the RAM at Step 315 and obtains all of them as pixels to be evaluated (Step 125).

Then, the CPU 2 color converts the color space of the pixel to be evaluated from the RGB space to the YIQ space (Step 130), calculates the average value Qm by averaging the Q-values of the pixels (Step 135) and outputs it as a pulse wave signal (Step 140).

Subsequently, the second adjustment processing at Step 145 will be explained.

The processing from Step 100 to Step 140 including the first adjustment processing is processing to 1 frame obtained from the moving image at Step 30 in FIG. 4, and Qm including the pulse wave component to the 1 frame image is calculated.

On the other hand the adjustment processing is processing for detecting a pulse wave signal from the Qm raw signal obtained from a continuous plurality of frame images more efficiently and adjusts initial values of the range Slo to Shi of the skin color data. The initial values Slo and Shi to be targets of the second adjustment processing are values read out of the skin color data of the user database 14 at Step 300 in FIG. 23 and stored in the RAM 4.

Here, a principle of the second adjustment processing will be explained by FIGS. 24 to 26.

FIG. 24 are a principle explanatory view in a case where a peak value of disturbance is large, and FIG. 25 are a principle explanatory view in a case where a peak value of the pulse wave is small.

Upper stages in FIGS. 24 and 25 illustrate narrowed-down pixels (pixels to be evaluated) of a plurality of frame images, middle stages illustrate raw signals of the pulse wave according to a temporal change of a plurality of Qm values acquired from pixels to be evaluated, and lower stages illustrate spectral density (PSD: Power Spectral Density) of the raw signals of the pulse wave.

In the second adjustment processing, spectral density for each frequency is acquired from the raw signal of the pulse wave by the plurality of Qm values, and on the basis of the peak value in a frequency range which can be assumed to be disturbance and a peak value in a frequency range which can be assumed to be a signal within a pulse wave detection range, the range Slo to Shi (initial values stored in the RAM 4) of the skin color data when the narrowing-down with the S component is made for each frame image is adjusted.

The spectral density of the actual pulse wave signal has an upper limit frequency F in its frequency.

Thus, as illustrated on the lower stages in FIGS. 24 and 25, by acquiring the spectral density K of the raw signal, it can be determined that a portion at the upper limit frequency F or less corresponds to the pulse wave signal, and a portion exceeding the upper limit frequency F corresponds to the disturbance.

Then, as illustrated on the lower stage in FIG. 24(a), when a peak value k1 of the disturbance portion exceeding the upper limit frequency F is larger than a predetermined disturbance reference value C1, as illustrated on the middle stage in FIG. 24(a), since the disturbance portion is included in a large quantity, the pulse wave cannot be detected accurately.

Thus, in order to decrease the disturbance component, the peak value k1 of the disturbance portion is lowered by narrowing the range Slo to Shi of the skin color data used as the initial values at Step 300.

By repeating the adjustment of the range Slo to Shi to the 1 frame image, unlike the first adjustment for acquiring the optimal range for the frame image, in the second adjustment processing in which Qm of the plurality of frame images are targets, adjustment of the initial value range Slo to Shi is made once and is reflected in the subsequent frame image.

As a result, having gone through the second adjustment processing for the plurality of frame images, as illustrated on the lower stage in FIG. 24(b), a peak value k2 of the disturbance portion falls to the disturbance reference value C1 or less.

On the other hand, as illustrated on the lower stage in FIG. 25(a), when a peak value k3 of the pulse wave signal at the upper limit frequency F or less is smaller than a predetermined pulse wave reference value C2, as illustrated on the middle stage in FIG. 25(a), a change range of the raw signal (Qm) is too small to detect the pulse wave signal.

This is considered to be caused by excessive narrowing-down with the S component and thus, in order to increase the change range of the raw signal, by widening the range Slo to Shi of the skin color data used as the initial values at Step 300 in FIG. 23, the peak value k3 of the pulse wave signal portion is increased.

As a result, having gone through the second adjustment processing for the plurality of frame images, as illustrated on the lower stage in FIG. 25(b), a peak value k4 of the disturbance portion reaches the pulse wave reference value C2 or more.

FIG. 26 are an explanatory view on an adjustment range in the second adjustment processing.

Figure 26A:
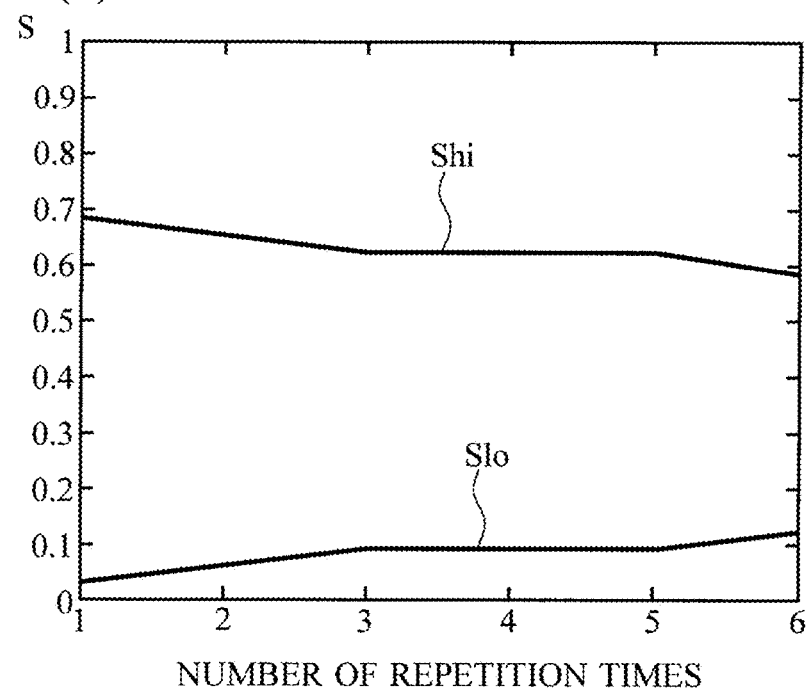
FIG. 26 are an explanatory view for an adjustment range in the second adjustment processing.
Figure 26B:
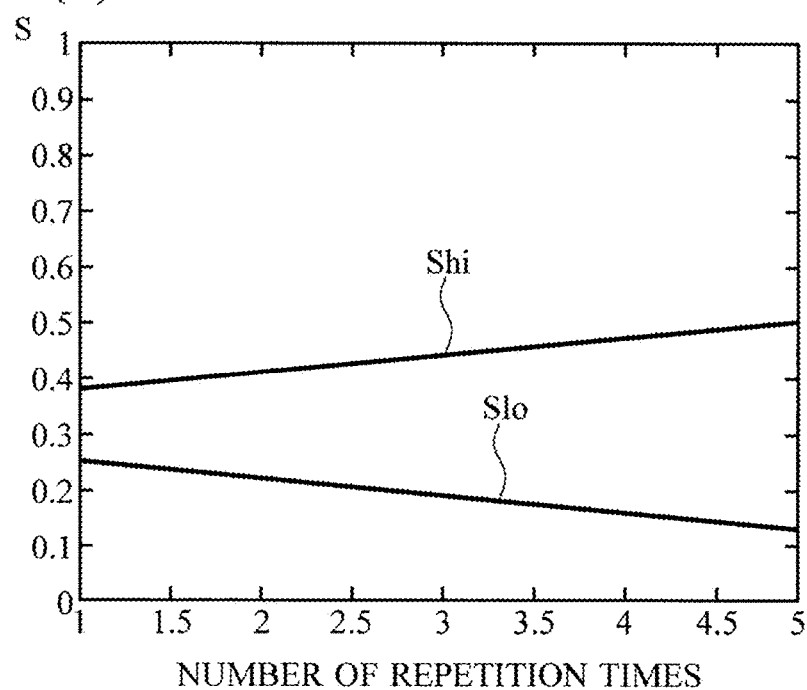

FIGS. 26(a) and 26(b) correspond to FIGS. 4 and 25, respectively, and illustrate an example of decreasing and increasing the range Slo to Shi of the initial values of the S component.

In the first adjustment processing, the adjustment is performed a plurality of times until the condition is satisfied for 1 frame image (Steps 332 and 340 in FIG. 23). Since the second adjustment processing is one session of adjustment, the adjustment range is set larger than that of the first adjustment processing. In this embodiment, Slo and Shi are increased/decreased by 0.02 each in one session of the adjustment processing. That is because the peak value k1 of the disturbance portion is to become the disturbance reference value C1 or less (k2) earlier and the peak value k3 of the pulse wave signal portion is to become the pulse wave reference value C2 or more (k4) in the first adjustment processing for the subsequent frame image.

It is to be noted that, the ranges of increase/decrease of Slo and Shi are examples and can be changed or adjusted as appropriate and moreover, the ranges of the increase and decrease do not have to be the same, and different values may be employed. This point also applies to the first adjustment processing.

The disturbance reference value C1 for the peak value of the disturbance portion and the pulse wave reference value C2 for the peak value of the pulse wave signal portion are both values determined experimentally in advance and are different depending on a calculation method of the spectral density or a length used in the calculation.

In this embodiment, the spectral density is calculated by 128-point Welch method spectral density estimation, and the disturbance reference value C1 is 60 and the pulse wave reference value C2 is 100, but the other values may be naturally employed.

Subsequently, details of the second adjustment processing (Step 145) in FIG. 19 will be explained.

Figure 27:
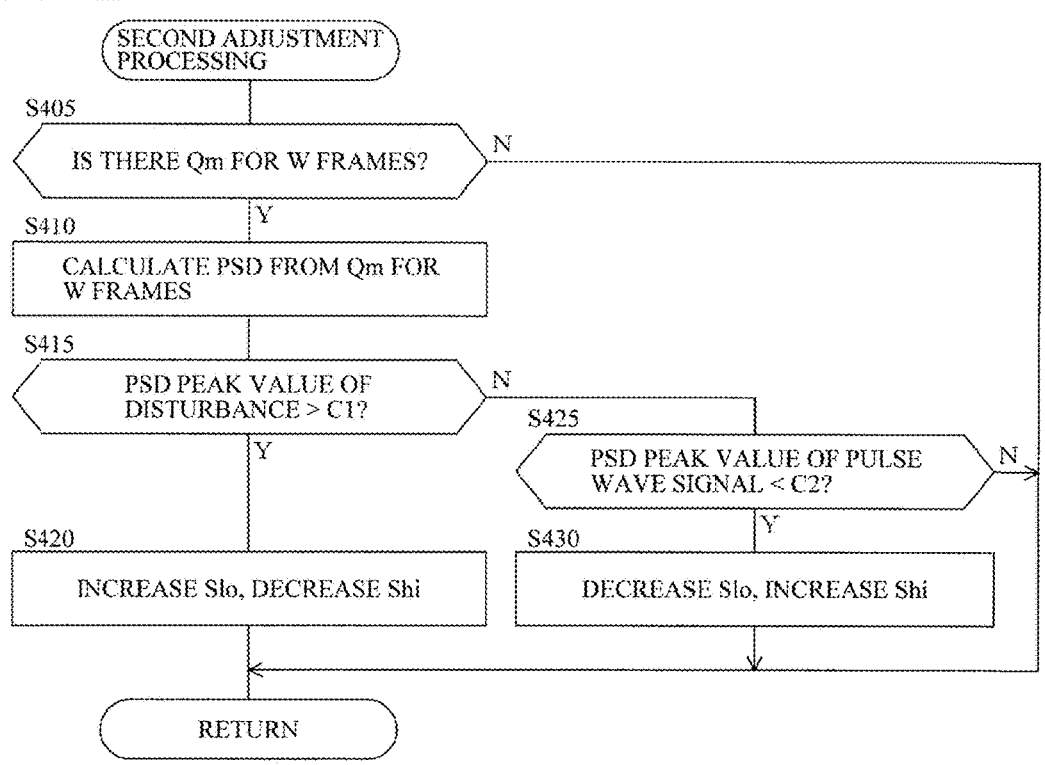
FIG. 27 is a flowchart of the second adjustment processing.

FIG. 27 is a flowchart of the second adjustment processing.

The CPU 2 determines whether there is Qm for W frames (Step 405). That is, the CPU 2 determines whether the number of Qm output at Step 140 (FIG. 19) is not smaller than W. Here, the value of W is arbitrary as long as it is not smaller than the number capable of estimating the pulse wave, but it is set to W=60 in this embodiment.

When there is no Qm for W frames (Step 405; N), the CPU 2 cannot make determination on the pulse wave and returns. As a result, the routine proceeds to processing for the subsequent frame image (Step 30 in FIG. 4).

On the other hand, when there are Qm for the W frames (Step 405; Y), the CPU 2 calculates the spectral density (PSD) from Qm for the latest W frames (Step 410). That is, the spectral density K on the lower stages in FIGS. 24 and 25 are acquired.

Then, the CPU 2 determines whether the PSD peak value of the disturbance portion is larger than the disturbance reference value C1 or not (Step 415). That is, in the example in FIG. 24(a), the CPU 2 acquires the peak value k1 of the disturbance portion larger than the upper limit frequency Fin the calculated spectral density K and determines whether this peak value is larger than the disturbance reference value C1 or not.

If the peak value of the disturbance portion is larger than the disturbance reference value C1 (Step 415; Y), the CPU 2 increases Slo and decreases Shi which are the initial values of the S component stored in the RAM 4 (Step 420) and returns to the main routine.

On the other hand, if the peak value of the disturbance portion is not larger than C1 (Step 415; N), the CPU 2 determines whether the peak value of the pulse wave signal portion is smaller than the pulse wave reference value C2 or not (Step 425).

If the peak value of the pulse wave signal portion is less than C2 (Step 425; Y), the CPU 2 decreases Slo and increases Shi which are the initial values of the S component stored in the RAM 4 (Step 430), and returns to the main routine.

Moreover, if the peak value of the pulse wave signal portion is C2 or more (Step 425; N), the CPU 2 returns to main routine.

As described above, according to the fourth embodiment, it is to be noted that, regarding specification of the skin portion, by specifying the candidate pixel by using the H component and by narrowing down the candidate pixel as a target by using the S component, more accurate specification of the skin portion can be made possible. That is, in determining the evaluation region for acquiring Qm, by determining the candidate pixel by the H component of the frame image and by narrowing down the candidate signal by the S component, the skin portion (evaluation region) is specified with higher accuracy.

Moreover, in the first adjustment processing of narrowing down by the S component, by increasing/decreasing the range Slo to Shi repeatedly until the optical narrowing-down range is obtained for 1 frame image, narrowing-down based on the optimal range can be made.

Furthermore, in the second adjustment processing, by acquiring the spectral density for the raw signal acquired from a plurality of the frame images, the range of the initial values Slo and Shi for narrowing-down for the subsequent frame image is narrowed when the peak value of the disturbance portion is large, while the range of the initial values is widened when the peak value of the pulse wave signal portion is small. As described above, by adjusting the initial value of the S component used for narrowing-down, the processing for the frame image and after (the number of repetition times of the first adjustment processing) can be reduced, and high-speed processing is realized.

In the fourth embodiment described above, the case where the first adjustment processing and the second adjustment processing are both executed is explained, but either one of them may be omitted and the other may be employed.

When only the second adjustment processing is to be employed, since there is no first adjustment processing, the adjustment range is preferably taken smaller than the embodiments explained above. For example, the case where the initial values Slo and Shi are increased/decreased by 0.02 each is explained, but it may be an increase/decrease by 0.1 each or 0.005 each. However, this increase/decrease range is arbitrary.

Moreover, in the fourth embodiment explained above, the case where the first adjustment processing and the second adjustment processing are added to the first embodiment is explained, but the fourth embodiment may be applied to the second embodiment or the third embodiment.

EXPLANATIONS OF LETTERS OR NUMERALS 1 pulse wave detection device
2 CPU
3 ROM
4 RAM
5 display unit
6 input unit
7 output unit
8 camera
9 storage unit
10 user
12 pulse wave detection program
14 user database
15 camera characteristic data
20 nose region
21 hair
22 eyebrow
23 eye
24 lip
25 background
26 skin portion
30 still image
31 frame image
32 HSV image
35 pulse wave
41, 42 period
45 eye portion
46 white eye portion
47 iris portion
48 pupil portion
51 brightness signal
52 before correction pulse wave signal
53 after correction pulse wave signal
55 eye region
61 left region
62 center region
63 right region
101 evaluation region
102 background

The invention claimed is:

1. A pulse wave detection device comprising:
a camera that obtains a moving image;
a central processing unit (CPU) programmed to:
obtain the moving image from the camera, taking from the moving image a region including at least skin of a target;
specify a skin portion of the target shown on the obtained moving image;

obtain a pulse wave of the target from a temporal change of a predetermined color space component in the specified skin portion; and output the obtained pulse wave, wherein the predetermined color space component is a chromaticity component in a YIQ color space including a brightness component and chromaticity components.

2. The pulse wave detection device according to claim 1, wherein the region includes at least the skin of the target includes the face of the target.

3. The pulse wave detection device according to claim 1, wherein the CPU is further programmed to:

register a reference component which is the color space component to be a reference for specifying the skin portion of the target; and specify a portion where the predetermined color space component corresponds to the registered reference component in the moving image as the skin portion.

4. The pulse wave detection device according to claim 1, wherein the color space component used by the CPU to specify the skin portion and the color space component used by the pulse wave obtaining means for obtaining the pulse wave are different color space components.

5. The pulse wave detection device according to claim 4, wherein the color space component used by the CPU to specify the skin portion is a hue component of an HSV color space made of the hue component, a saturation component, and a brightness component.

6. The pulse wave detection device according to claim 1, wherein the CPU is further programmed to:

convert a color space of the moving image; and obtain a color space component in the color space obtained by converting the color space of the moving image.

7. The pulse wave detection device according to claim 3, wherein the camera obtains a face image, and the CPU is further programmed to:

obtain the face image from the camera;

specify a predetermined region where skin of the face is exposed by face recognition processing in the obtained face image; and register the color space component of the specified region as the reference component.

8. The pulse wave detection device according to claim 7, wherein the predetermined region is a nose region of the target.

9. The pulse wave detection device according to claim 7, wherein the CPU is further programmed to:

register a value obtained by applying statistical processing to distribution of the color space component in the specified region.

10. The pulse wave detection device according to claim 1, wherein the CPU is further programmed to:

specify the skin portion by the pixel values of the moving image.

11. The pulse wave detection device according to claim 1, wherein the target is a passenger of transportation equipment and a physical condition of the passenger is monitored by using the output pulse wave.

12. A non-transitory computer-readable medium storing a pulse wave detection program causing a computer to execute a process, the process comprising:

obtaining a moving image taking from the moving image a region including at least skin of a target;

specifying a skin portion of the target shown on the obtained moving image;

obtaining a pulse wave of the target from a temporal change of a predetermined color space component in the specified skin portion; and outputting the obtained pulse wave, wherein the predetermined color space component is a chromaticity component in a YIQ color space including a brightness component and chromaticity components.

13. The pulse wave detection device according to claim 5, wherein the CPU is further programmed to:

specify the skin portion by specifying a skin portion candidate with the hue component of the HSV color space and narrows down the skin portion candidate with the saturation component.

14. The pulse wave detection device according to claim 13, wherein the CPU is further programmed to:

specify the skin portion for each frame image constituting the obtained moving image; and obtain the pulse wave from a temporal change of the chromaticity component corresponding to the skin portion specified for each frame image.

15. The pulse wave detection device according to claim 14, wherein the CPU is further programmed to:

perform narrowing-down by using a lower limit value and an upper limit value of the saturation component registered in advance.

16. The pulse wave detection device according to claim 15, wherein the CPU is further programmed to:

set the lower limit value and the upper limit value registered in advance to initial values;

estimate a face region from the specified skin portion candidate;

widen a range of the lower limit value and upper limit value when the number of pixels of the face region is less than a first predetermined threshold value;

perform the narrowing-down of the skin portion candidate again with the lower limit value and the upper limit value after widening; and repeat the narrowing-down again until the number of the pixels of the face region reaches the first predetermined threshold value or more.

17. The pulse wave detection device according to claim 16, wherein the CPU is further programmed to:

narrow down the range of the lower limit value and upper limit value when the estimated number of pixels other than the face region is larger than a second predetermined threshold value;

perform the narrowing-down of the skin portion candidate again by the lower limit value and the upper limit value after narrowing-down; and repeat the narrowing-down again until the number of pixels other than the face region reaches the predetermined threshold value or less.

18. The pulse wave detection device according to claim 15, wherein the CPU is further programmed to:

acquire spectral density with respect to a temporal change of the chromaticity component for the plurality of frame images and for changing the lower limit value and the upper limit value registered in advance on the basis of a peak value of a predetermined frequency region with the spectral density; and specify the skin portion for the frame image and after by using the lower limit value and the upper limit value after being changed.

\* \* \* \* \*